(12) United States Patent
Yamamoto et al.

(10) Patent No.: US 9,372,143 B2
(45) Date of Patent: Jun. 21, 2016

(54) SCANNING IMAGE FLOW CYTOMETER

(71) Applicant: CAPTL LLC, West Lafayette, IN (US)

(72) Inventors: Masanobu Yamamoto, West Lafayette, IN (US); J. Paul Robinson, West Lafayette, IN (US)

(73) Assignee: CAPTL LLC, West Lafayette, IN (US)

( * ) Notice: Subject to any disclaimer, the term of this patent is extended or adjusted under 35 U.S.C. 154(b) by 404 days.

(21) Appl. No.: 13/894,521

(22) Filed: May 15, 2013

(65) Prior Publication Data
US 2014/0339446 A1 Nov. 20, 2014

(51) Int. Cl.
*G01N 15/14* (2006.01)

(52) U.S. Cl.
CPC ........ *G01N 15/1434* (2013.01); *G01N 15/1429* (2013.01)

(58) Field of Classification Search
CPC .......... G01N 15/1429; G01N 15/1434; G01N 15/14; G01N 15/1436; G01N 2015/1006; G01N 2015/144; G01N 2015/1445
See application file for complete search history.

(56) References Cited

U.S. PATENT DOCUMENTS

| | | | |
|---|---|---|---|
| 3,918,812 A | 11/1975 | Holm | |
| 4,573,796 A * | 3/1986 | Martin | G01N 15/1429 250/461.2 |
| 4,920,275 A | 4/1990 | Itoh | |
| 4,999,513 A | 3/1991 | Ito | |
| 5,017,497 A | 5/1991 | Gerard de Grooth et al. | |
| 5,294,806 A * | 3/1994 | Batchelder | G01N 15/0205 250/565 |
| 5,644,388 A | 7/1997 | Maekawa | |
| 5,793,485 A | 8/1998 | Gourley | |
| 5,824,269 A | 10/1998 | Kosaka | |
| 6,608,680 B2 | 8/2003 | Basiji et al. | |
| 6,642,018 B1 | 11/2003 | Koller et al. | |
| 7,190,832 B2 * | 3/2007 | Frost | G01N 15/147 382/103 |
| 7,315,357 B2 * | 1/2008 | Ortyn | C12Q 1/6816 356/318 |
| 7,800,742 B2 * | 9/2010 | Fukuda | G01N 15/147 356/317 |

(Continued)

FOREIGN PATENT DOCUMENTS

| | | |
|---|---|---|
| EP | 0950890 A2 | 10/1999 |
| WO | WO03016875 A2 | 2/2003 |

(Continued)

OTHER PUBLICATIONS

Goda et al., "Hybrid dispersion laser scanner", in the Journal of Scientific Reports, vol. 2, Jun. 8, 2012, 8 pages.

(Continued)

*Primary Examiner* — John Lee
(74) *Attorney, Agent, or Firm* — Christopher J. White; Lee & Hayes, PLLC

(57) ABSTRACT

An image flow cytometer has a flow chamber with a flow channel formed therein to permit a microparticulate sample to flow through the flow channel. An irradiation optical system irradiates the sample in the channel with incident light in an irradiation spot smaller than a selected representative size, e.g., smaller than the sample. The system scans an irradiation position perpendicular to the flow direction of the sample. A detection optical system is opposed to the irradiation optical system through the flow chamber, or is off the optical axis of the incident light. The detection system detects a light intensity of resultant light from the flow chamber. A control unit detects the microparticulate sample according to a change of the light intensity of the resultant light detected by the detection optical system.

20 Claims, 28 Drawing Sheets

(56) References Cited

U.S. PATENT DOCUMENTS

| | | | |
|---|---|---|---|
| 7,800,754 B2* | 9/2010 | Kenyon | G01N 15/14 356/337 |
| 8,159,670 B2 | 4/2012 | Vacca et al. | |
| 8,400,632 B2 | 3/2013 | Vacca et al. | |
| 8,660,332 B2 | 2/2014 | Ortyn et al. | |
| 2002/0030811 A1* | 3/2002 | Schindler | G01N 21/6452 356/318 |
| 2002/0113204 A1 | 8/2002 | Wang | |
| 2002/0123033 A1* | 9/2002 | Eyal | G01L 3/5027 435/4 |
| 2003/0007894 A1 | 1/2003 | Wang | |
| 2004/0067167 A1 | 4/2004 | Zhang et al. | |
| 2005/0046848 A1 | 3/2005 | Cromwell et al. | |
| 2005/0057749 A1 | 3/2005 | Dietz et al. | |
| 2005/0068536 A1* | 3/2005 | Schwabe | B01L 3/502715 356/436 |
| 2005/0122522 A1* | 6/2005 | Padmanabhan | G01B 11/272 356/436 |
| 2007/0109530 A1* | 5/2007 | Ueno | G01N 15/1404 356/39 |
| 2007/0171778 A1 | 7/2007 | Saito et al. | |
| 2009/0122311 A1* | 5/2009 | Kanda | G01N 21/51 356/318 |
| 2009/0298703 A1* | 12/2009 | Gough | G06T 7/0012 506/8 |
| 2010/0021039 A1* | 1/2010 | Ortyn | G01J 3/2889 382/134 |
| 2010/0120077 A1* | 5/2010 | Daridon | B01L 3/502738 435/29 |
| 2010/0172020 A1 | 7/2010 | Price | |
| 2010/0231913 A1* | 9/2010 | Tsukii | G01N 21/645 356/436 |
| 2010/0238442 A1 | 9/2010 | Heng | |
| 2011/0066382 A1* | 3/2011 | Adams | G01N 15/147 702/19 |
| 2011/0069310 A1* | 3/2011 | Muraki | G01N 15/14 356/335 |
| 2011/0085221 A1 | 4/2011 | Ortyn et al. | |
| 2011/0169837 A1* | 7/2011 | Takata | G01N 15/14 345/440.2 |
| 2011/0192991 A1* | 8/2011 | Fukumoto | G01J 3/1256 250/459.1 |
| 2011/0216319 A1* | 9/2011 | Schwabe | B01L 3/502715 356/338 |
| 2012/0070818 A1 | 3/2012 | Rowlen et al. | |
| 2012/0103112 A1* | 5/2012 | Vrane | G01N 15/1404 73/864.35 |
| 2012/0136584 A1* | 5/2012 | Ban | G01N 15/1429 702/21 |
| 2012/0139917 A1* | 6/2012 | Suzuki | G01N 15/1429 345/420 |
| 2012/0220022 A1 | 8/2012 | Ehrlich et al. | |
| 2012/0270306 A1 | 10/2012 | Vacca et al. | |
| 2012/0281216 A1* | 11/2012 | Ilkov | G01N 21/53 356/416 |
| 2012/0287435 A1* | 11/2012 | Adams | G01N 21/51 356/340 |
| 2012/0293797 A1 | 11/2012 | Braeckmans | |
| 2012/0295339 A1* | 11/2012 | Wu | G01N 15/1459 435/286.2 |
| 2013/0050782 A1* | 2/2013 | Heng | G01N 15/1434 358/494 |
| 2013/0091937 A1* | 4/2013 | Rich | G01N 15/1404 73/61.71 |
| 2014/0339446 A1* | 11/2014 | Yamamoto | G01N 15/1429 250/576 |

FOREIGN PATENT DOCUMENTS

| | | |
|---|---|---|
| WO | 2007121179 | 10/2007 |
| WO | WO2013054502 | 4/2013 |

OTHER PUBLICATIONS

PCT Search Report dated Sep. 26, 2014 for Application No. PCT/US2014/037995, 3 pages.

Koller et al., "High-Throughput Laser Mediated In Situ Cell Purification With High Purity and Yield", Cytometry Part A, No. 61, 2004, pp. 153-161.

PCT Written Opinion and International Search Report dated Sep. 26, 2014 for Application No. PCT/US2014/037995, 11 pages.

Vacca et al., "Laser Rastering Flow Cytometry: Fast Cell Counting and Identification", in the Proceedings of SPIE Bios: Biomedical Optics, International Society for Optics and Photonics, 2009, 11 pages.

Carl Zeiss Microscopy GmbH, "LSM 710—The Power of Sensitivity—A New Dimension in Confocal Laser Scanning Microscopy," 07745 Jena, Germany, BioSciences, nnicroscopy@zeiss.com (www.zeiss.com/microscopy), 32 pages.

Fulwylver, Mack J. et al., "Device Which Separates Minute Particles According to Electronically Sensed Volume," Review of Scientific Instruments, Citation: (Rev. Sci. Instrum. 40, 42 (1969); doi: 10.1063/1.1683746), online at http://dx.doi.org/10.1063/1.1683746, 8 pages.

Mullaney, P. F. et al., "Cell Sizing: A Light Scattering Photometer for Rapid Volume Determination," Review of Scientific Instruments, (Rev. Sci. Instrum. 40, 1029, (1969); doi: 10.1063/1.1684143), online at http://dx.doi.org/10.1063/1.1684143, 5 pages.

Fulwylver, M. J., LA-3432-MS "An Electronic Separator with Potential Biological Separation," Los Alamos Scientific Laboratory of the Univ. Of California, Los Alamos, New Mexico, Biological and Medical Research Group (H-4) of the Health Division—Annual Report, Jul. 1964 through Jun. 1965, written Jul. 1965, Contributed by Bob Auer, 6 pages.

Los Alamos Scientific Laboratory of the Univ. Of California, LA-3848-MS, UC-48, Biology and Medicine TID-4500, Los Alamos, New Mexico, Biological and Medical Research Group (H-4) of the Health Division—Annual Report, Jul. 1966 through Jun. 1967, written Sep. 1967, Contributed by Bob Auer, 14 pages.

Kay, D. B. et al., "Experimental Findings on Gynecologic Cell Orientation and Dynamics for Three Flow Nozzle Geometries," Journal of Histochemistry & Cytochemistry, http://jhc.sagepub.com/, online at http://jhc.sagepub.com/content/25/7/870, 6 pages. (1977).

Fulwylver, M. J., "Electronic Separation of Biiological Cells by Volume," Science, New Series, vol. 150, No. 3698 (Nov. 12, 1965), pp. 910-911, published by American Association for the Advancement of Science, http://www.jstor.org/stable/1717506, accessed: Aug. 5, 2013 13:38, 3 pages.

Van Dilla, M. A., et al., "Cell Microfluoremetry: A Method for Rapid Fluorescence Measurement," Science, New Series, vol. 163, No. 3872 (Mar. 14, 1969), pp. 1213-1214, published by American Association for the Advancement of Science, http://www.jstor.org/stable/1726554, accessed: Aug. 5, 2013 13:28, 3 pages.

Eisert, W. G., "High Resolution Optics Combined with High Spatial Reproducibility in Flow," Cytometry, vol. 1, No. 4, pp. 254-259, (#0196-4763/81/0104-0254$00.00/0), Nov. 25, 1979, 6 pages total.

Kumbhakar, Manoj et al., Abstract of "Single-Molecule Detection in Exploring Nanoenvironments: An Overview, Journal of Photochemistry and Photobiology C: Photochemistry Reviews," vol. 5, Issue 2, Oct. 15, 2004, pp. 113-137, ISSN 1389-5567, http://dx.doi.org/10.1016/j.jphotochemrev.2004.07.004, (http://www.sciencedirect.com/science/article/pii/S1389556704000206) total 3 pgs.

Kim, et al., "An efficient 3-dimensional hydrodynamic focusing microfluidic device by means of locally increased aspect ratio", Microelectronic Engineering, vol. 86, No. 4-6, Apr. 1, 2009, Elsevier Publishers, pp. 1343-1346.

PCT Search Report and Written Opinion mailed Sep. 14, 2015 for PCT Application No. PCT/US14/71391, 15 pages.

Simonnet, et al., "Two-dimensional hydrodynamic focusing in a simple microfluidic device", Applied Physics Letters, American Institute of Physics, US, vol. 87, No. 11, Sep. 8, 2005, pp. 114104-1 to 114104-3.

(56) References Cited

OTHER PUBLICATIONS

Sundararajan, et al., "Three-Dimensional Hydrodynamic Focusing in Polydimethylsiloxane (PDMS) Microchannels", Journal of Microelectromechanical Systems, vol. 13, No. 4, Aug. 1, 2004, IEEE, pp. 559-56.

Zhuang, et al., "Detection of unlabeled particles in the low micrometer size range using light scattering and hydrodynamic 3D focusing in a microfluidic system", Electrophoresis, vol. 33, No. 12, Jul. 28, 2012, pp. 1715-1722.

Doohan, James, "Blood Cells," retrieved on Feb. 12, 2016, at <<http://www.biosbcc.net/doohan/sample/htm/Blood%20cells.htm>>, Biological Sciences BioMed 108 Human Physiology, 2000, 6 pages.

Newport: "Focusing and Collimating," retrieved on Dec. 4, 2015, at <<http://www.newport.com/Focusing-and-Collimating/141191/1033/content.aspx>>, 3 pages.

Mahon, et al., "Blood Cell Identification," retrieved on Dec. 4, 2015, at <<http://www.depts.ttu.edu/liru_afs/staff/dailey/jwdblood.htm>>, 1 page.

Spectra-Physics: SP-120 Manual, retrieved on Dec. 4, 2015, at <<https://web.archive.org/web/20041227095059/http://lasers.757.org/manuals/Spectra_Physics_120-256/p44.JPG>>, 12 pages.

\* cited by examiner

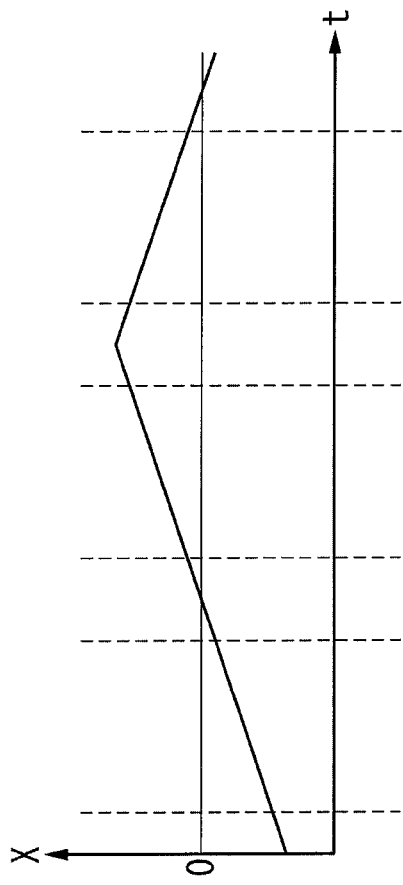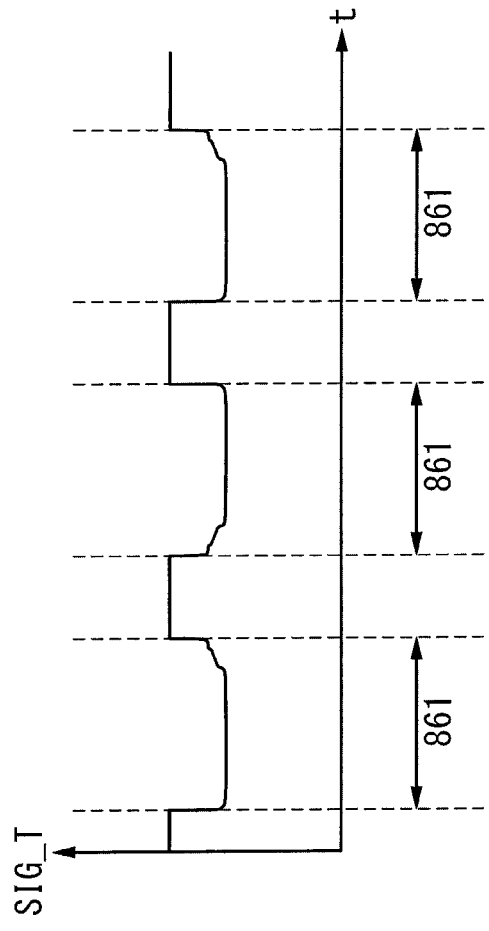

SCANNING IMAGE FLOW CYTOMETER

TECHNICAL FIELD

The present invention relates to flow cytometry, and particularly to image flow cytometers.

BACKGROUND

In the fields related to life sciences such as genetics, immunology, molecular biology, and environmental science, flow cytometry is widely used to analyze microparticulate samples such as living cells, yeast, and bacteria. Particles or cells from 500 nm up to 50 micron can generally be measured in flow cytometry. In general, in the case of analyzing a cell or the like with a flow cytometer, a label made of a fluorescent substance is attached to the surface of a cell to be analyzed. Next, a liquid such as water or saline is used to move the labeled cell through a flow channel of a flow chamber, which is an area in which the labeled cell is to be analyzed, and laser light having a relatively high output is radiated towards a predetermined position to irradiate the cell. Then, forward-scattered light and side-scattered light, which are generated due to the size and structure of each cell, and fluorescence, which is generated by excitation light irradiation, are observed. In the case of observing fluorescence from a cell, a configuration for spectral analysis of the fluorescence condensed in a direction other than an irradiation path of excitation light is widely used to avoid adverse effects of transmitted or scattered excitation light. Fluorescent substances to be attached or combined for each type of cells are known. Accordingly, the wavelength and intensity of the fluorescence are observed and the intensity component to be superimposed is compensated to thereby identify the type of each cell flowing through the flow channel.

It is necessary to individually perform measurement of cells or the like with laser light. A large number of microparticulate samples are supplied to a flow chamber through a tube from a container such as a vial containing the samples. The flow chamber is generally configured to permit microparticulate samples to be aligned and flow by a method called hydrodynamic focusing.

Hydrodynamic focusing will be briefly described. When using hydrodynamic focusing, a sample flow including microparticulate samples is discharged from an elongated nozzle. The discharged sample flow is surrounded by a sheath flow of, e.g., water or saline, which is an isosmotic fluid, and flows through the flow channel of the flow chamber. The discharge pressure of the sample flow is set to be higher than that of the sheath flow, thereby permitting the microparticulate samples, which are randomly distributed, to be aligned and flow in the sample flow. This phenomenon is called a three-dimensional (3-D) laminar flow in terms of fluid dynamics. This makes it possible to radiate laser light independently towards each microparticulate sample, such as a cell, and to detect and analyze the scattered light and excited fluorescence.

Next, a typical flow cytometry system ("flow cytometer") will be described. A typical flow cytometer includes a laser light irradiation optical system, a flow chamber, a detection optical system, and a control unit. The laser light irradiation optical system radiates laser light onto microparticulate samples within the flow chamber. The laser light irradiation optical system includes one or more lasers that output laser light having a wavelength corresponding to a label to be excited, and a condensing optical system that condenses the laser light on the flow chamber. The detection optical system can detect an intensity of light such as transmitted light, scattered light, and fluorescence from the microparticulate samples.

For example, consideration is given to the case where laser light is radiated in the vicinity of an orifice in a so-called jet-in-air system in which a stream is discharged through the orifice of a flow chamber. In this case, when laser light is radiated onto a stream having a cylindrical sectional shape from a direction substantially perpendicular to the section, the stream acts as a cylindrical lens. Accordingly, the laser light is radiated onto the microparticulate samples as a flat, elliptic beam in a direction perpendicular to the stream. An irradiation spot of laser light can have a substantially elliptical shape of 10 μm (minor axis)×70 μm (major axis), or other shapes or sizes. The irradiation spot is, e.g., an area of a microparticulate sample onto which enough laser light falls that characteristics of the microparticulate sample can be determined. Also in the case of using a flow chamber, which is called a cuvette, a flat beam having substantially the same width as that of a stream is used to observe particulate objects, e.g., microparticulate samples. Note that in the case of radiating a plurality of laser beams having different wavelengths, irradiation spots are generally disposed separately from each other in a flow direction for each wavelength so as to reduce stray light between the laser beams having different wavelengths.

When the flowing microparticulate samples pass through laser irradiation spots, scattered light and fluorescence, which is caused due to excitation of a labeled substance, are generated. The scattered light includes forward-scattered light having a small scattering angle which represents a size of a fine particle, and side-scattered light having a large scattering angle which represents an internal structure of a fine particle. Each of the forward-scattered light, the side-scattered light, and the fluorescence is detected by a photodetector of the detection optical system. The fluorescence has a small intensity and is radiated uniformly over the whole solid angle. For this reason, the fluorescence is condensed by a condenser lens having a large numerical aperture, and is then detected by an ultrasensitive photodetector which is called a photomultiplier tube (PMT). Then, the control unit performs amplification, analog-digital conversion, and operation on the light signal detected by the photodetector.

Furthermore, the above-described flow cytometer is provided with a mechanism for fractional extraction (sorting) of microparticulate samples such as cells. As a typical method, an ultrasonic vibration is applied to a stream in the flow chamber to thereby divide the stream, which is discharged from the orifice, into droplets, so that each droplet contains the microparticulate sample. Then, based on the measurement by the control unit, positive or negative electric charges are applied to the droplets. The droplets having positive or negative electric charges are deflected in the opposite direction depending on the polarity of the electric charges, when passing through a high-intensity electric field. After that, the deflected droplets are collected. As a result, sorted cells can be extracted for each type, and only cells of a specific type necessary for analysis, culture, or the like can be obtained. A flow cytometer having such a fractional extraction function is called a sorter. A flow cytometer which does not have such a fractional extraction function but has only an analysis function is called an analyzer.

Reference is made to the following:

Patent Literature 1: "Control of flow cytometer having vacuum fluidics"—U.S. Pat. No. 5,395,588 A Patent Literature 2: "Method of aligning, compensating, and calibrating a flow cytometer for analysis of samples, and microbead standards kit therefor"—U.S. Pat. No. 5,093,234 A Patent Literature 3: "Method for analysis of cellular components of a fluid"—U.S. Pat. No. 5,047,321 A Patent Literature 4: "Apparatus for counting and/or measuring particles suspended in a fluid medium"—U.S. Pat. No. 4,056,324 A Patent Literature 5: "Apparatus for measuring cytological properties"—U.S. Pat. No. 4,225,229 A Patent Literature 6: "Orifice inside optical element"—U.S. Pat. No. 4,348,107 A Patent Literature 7: "Particle Separator"—U.S. Pat. No. 3,380,584

Reference is also made to U.S. Pat. No. 4,395,676, filed Nov. 24, 1980, issued Jul. 26, 1983, entitled "Focused aperture module"; to U.S. Pat. No. 4,487,320, filed Nov. 3, 1980, issued Dec. 11, 1984, entitled "Method of and apparatus for detecting change in the breakoff point in a droplet generation system"; to U.S. Pat. No. 4,498,766, filed Mar. 25, 1982, issued Feb. 12, 1985, entitled "Light beam focal spot elongation in flow cytometry devices"; and to U.S. Pat. No. 3,657,537, filed Apr. 3, 1970, issued Apr. 18, 1972, entitled "Computerized slit-scan cyto-fluorometer for automated cell recognition"; to U.S. Pat. No. 8,159,670 to Vacca et al.; to U.S. Publication No. 2005046848A1; to U.S. Publication No. 2005057749; to U.S. Publication No. 20120270306; and to U.S. Publication No. 2012220022, each of which is incorporated herein by reference.

Reference is also made to the following:

1. Fulwyler M J. "Electronic Separation of Biological Cells by Volume". *Science* 1965; 150: 910-911.
2. Fulwyler M J, Glascock, R B, Hiebert, R D, and Johnson N M. "Device which Separates Minute Particles According to Electronically Sensed Volume" 1969; *Rev. Sci. Inst:* 40: 42-48
3. Van Dilla M A, Mullaney P F, and Coulter J R. "Health Division Annual Report," Los Alamos Scientific Laboratory (July 1966-June 1967).
4. Van Dilla M A, Trujillo T T, Mullaney P., and Coulter J R. "Cell Microfluorometry: A New Method for the Rapid Measurement of biological Cells Stained with Fluorescent Dyes." *Science* 1969; 163: 1213-1214
5. Mullaney P F, Van Dilla M A, Coulter J R, and Dean P N. "A Light Scattering Photometer for Rapid Volume Determination." *Rev. Sci. Instr.* 1969; 40: 1029-1032
6. Kay and Wheeless, "Experimental findings on Gynecologic cell orientation and dynamics for three flow nozzle geometries." *J. Histochem. Cytochem* 1977, 25: 870

Further information about conventional flow cytometry can be found in Shapiro, H. M. *Practical Flow Cytometry*. John Wiley & Sons, Feb. 25, 2005.

SUMMARY

However, prior flow cytometers such as those described above have various problems or limitations. For example, the above-described flow cytometer performs spectral analysis of scattered light and fluorescence from microparticulate samples. As a result, the average size and the type of microparticulate samples can be discriminated and statistical analysis can be performed. However, prior cytometers cannot measure microstructures within a cell. Prior flow-cytometry schemes cannot measure the locations of fluorescent points within a microparticulate sample such as a cell. Prior schemes also cannot measure the shapes of microparticulate samples, such as two-dimensional (2-D) shapes or three-dimensional shapes.

Accordingly, various aspects described herein provide an image flow cytometer capable of observing a structure of each microparticulate sample. Various aspects permit doing so while maintaining a high throughput, i.e., measuring a large number of particles (or other microparticulate samples) per second.

An image flow cytometer for observing a microparticulate sample according to a first exemplary aspect includes a flow chamber including a flow channel formed therein to permit the microparticulate sample to flow through the flow channel in a flow direction; at least one irradiation optical system adapted to irradiate the microparticulate sample in the flow channel with incident light in an irradiation spot smaller than a selected representative size, and to scan an irradiation position of the irradiation spot substantially in a direction perpendicular to the flow direction; at least one detection optical system that detects a light intensity of resultant light from the flow chamber, the detection optical system being opposed to the irradiation optical system through the flow chamber or disposed at a position deviating from an optical axis of the incident light; and a control unit that detects the microparticulate sample according to a change of the light intensity of the resultant light detected by the detection optical system.

An image flow cytometer according to a second exemplary aspect of the present invention is the above-described image flow cytometer in which the irradiation optical system is adapted to cause the incident light to converge to a diffraction limit.

An image flow cytometer according to a third exemplary aspect of the present invention is the above-described image flow cytometer in which the control unit is adapted to cause the irradiation optical system to scan the irradiation position so that a focal point of the incident light passes through a center of a section of the micro flow channel perpendicular to the flow direction of the microparticulate sample.

An image flow cytometer according to a fourth exemplary aspect of the present invention is the above-described image flow cytometer in which the detection optical system is adapted to detect the resultant light including forward-scattered light or side-scattered light.

An image flow cytometer according to a fifth exemplary aspect of the present invention is the above-described image flow cytometer in which the irradiation optical system includes a laser, and the incident light is laser light.

An image flow cytometer according to a sixth exemplary aspect of the present invention is the above-described image flow cytometer in which the irradiation optical system includes a light deflector that deflects the incident light substantially along a direction perpendicular to the flow direction of the microparticulate sample in the micro flow channel in order to scan the irradiation position.

An image flow cytometer according to a seventh exemplary aspect of the present invention is the above-described image flow cytometer in which the light deflector is an acoustic optical deflector or an electro-optic deflector.

An image flow cytometer according to a eighth exemplary aspect of the present invention is the above-described image flow cytometer in which the control unit is adapted to: correlate a coordinate determined from a flow rate of the microparticulate sample and a rate of the scanning to the light intensity of the resultant light detected by the detection optical system; and obtain a two-dimensional distribution of the resultant light of the microparticulate sample.

An image flow cytometer according to a ninth exemplary aspect of the present invention is the above-described image flow cytometer in which the control unit is adapted to provide a two-dimensional image representing the two-dimensional distribution of the resultant light of the microparticulate sample.

An image flow cytometer according to a tenth exemplary aspect of the present invention is the above-described image flow cytometer in which a plurality of the detection optical systems are opposed to a plurality of the irradiation optical systems through the flow chamber, respectively; and the control unit is adapted to: obtain the two-dimensional distribution of the resultant light of the microparticulate sample from each of the plurality of the detection optical systems; and produce a three-dimensional distribution of the resultant light of the microparticulate sample by combining the obtained two-dimensional distributions of the resultant light of the microparticulate sample.

An image flow cytometer according to a eleventh exemplary aspect of the present invention is the above-described image flow cytometer in which the control unit is adapted to produce a three-dimensional image representing the three-dimensional distribution of the resultant light of the microparticulate sample.

An image flow cytometer according to a twelfth exemplary aspect of the present invention is the above-described image flow cytometer in which the cytometer includes a flow rate measurement unit that measures the flow rate of the microparticulate sample and outputs a measurement result to the control unit.

An image flow cytometer according to a thirteenth exemplary aspect of the present invention is the above-described image flow cytometer in which the control unit is adapted to sequentially update the flow rate of the microparticulate sample according to the measurement result from the flow rate measurement unit.

An image flow cytometer according to a fourteenth exemplary aspect of the present invention is the above-described image flow cytometer in which the flow rate measurement unit is disposed in the micro flow channel or is connected to the micro flow channel, and observes the flow rate of the microparticulate sample flowing through the micro flow channel.

An image flow cytometer according to a fifteenth exemplary aspect of the present invention is the above-described image flow cytometer in which the flow rate measurement unit includes the irradiation optical system and the control unit; the irradiation optical system includes a phase diffraction grating that provides the incident light including a plurality of diffracted light beams; the irradiation optical system directs the plurality of diffracted light beams to respective, different irradiation positions along the direction of flow of the micro flow channel; and the control unit is adapted to calculate the flow rate of the microparticulate sample from a distance between the irradiation positions of two diffracted light beams selected from the plurality of diffracted light beams; and a time difference obtained when the microparticulate sample passes through the irradiation positions.

An image flow cytometer according to a sixteenth exemplary aspect of the present invention is the above-described image flow cytometer in which the irradiation optical system is adapted to scan the respective irradiation positions substantially in a direction perpendicular to the flow direction.

An image flow cytometer according to a seventeenth exemplary aspect of the present invention is the above-described image flow cytometer in which the irradiation optical system is adapted to provide the incident light including a plurality of light beams; the irradiation optical system directs the plurality of light beams at respective, different angles to the irradiation position; the detection optical system is adapted to detect respective, separate light intensities of the resultant light corresponding to each of the light beams; and the control unit is adapted to compute a three-dimensional image of the microparticulate sample using the detected separate light intensities.

An image flow cytometer according to a eighteenth exemplary aspect of the present invention is the above-described image flow cytometer in which the irradiation optical system includes a light source and a diffraction grating that diffracts light from the source to provide the incident light including the plurality of light beams.

An image flow cytometer according to a nineteenth exemplary aspect of the present invention is the above-described image flow cytometer in which the irradiation optical system scans the irradiation position through an irradiation volume, and the micro flow channel is shaped so that only one of the microparticulate sample can be in the irradiation volume at one time.

According to exemplary aspects described herein, an image flow cytometer is capable of observing a structure of each microparticulate sample. Using a spot size of incident light smaller than the microparticulate sample permits measuring features, e.g., within a cell.

The above and other objects, features and advantages of the present invention will become more fully understood from the detailed description given herein below and the accompanying drawings which are given by way of illustration only, and thus are not to be considered as limiting the present invention.

BRIEF DESCRIPTION OF THE DRAWINGS

FIG. 8B is a graph showing an exemplary scanning position of an irradiation spot over time;

FIG. 8C is a graph showing an intensity of a detection signal SIG_T which is detected by a control unit 5 in an example;

Figure 1:
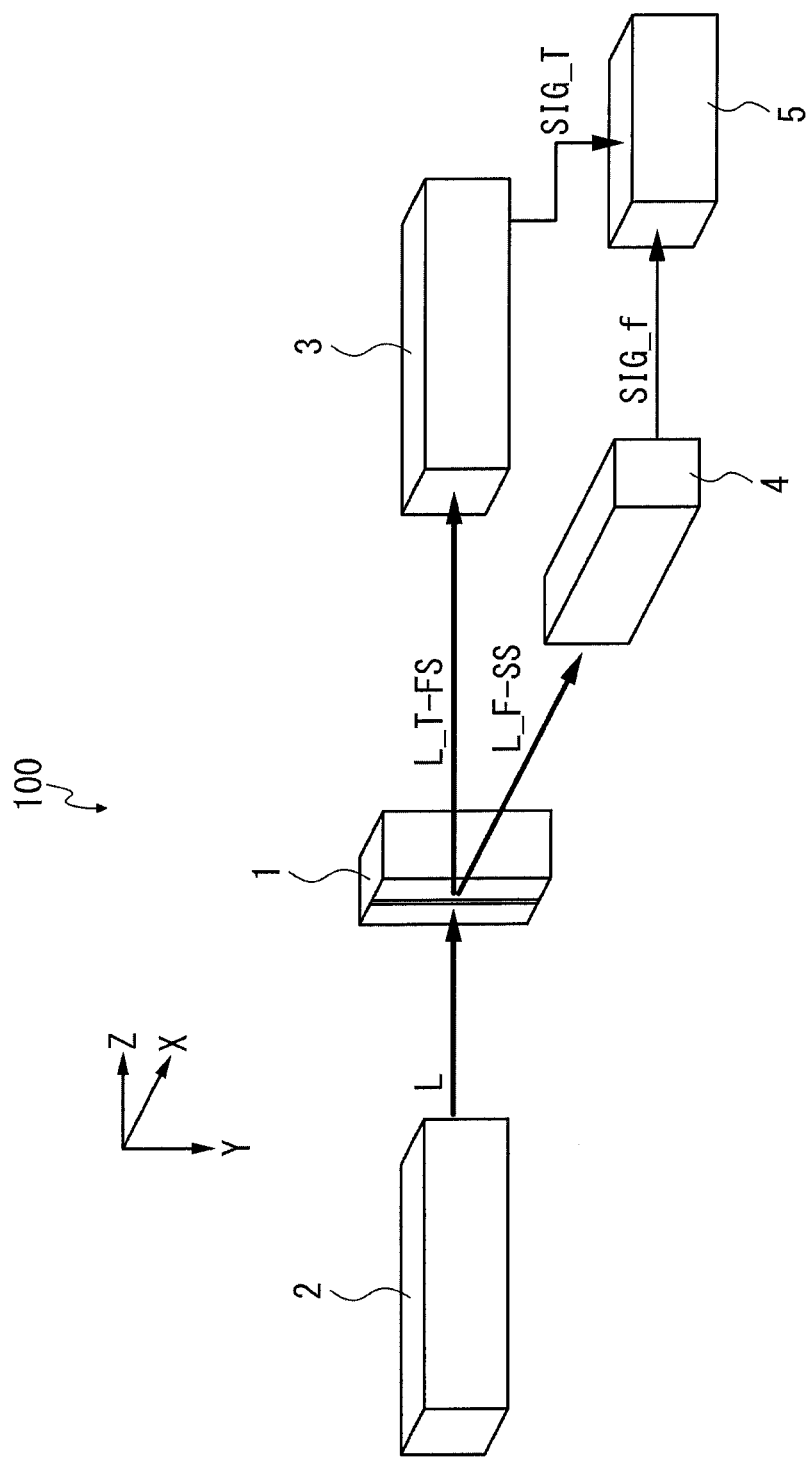
FIG. 1 is a configuration diagram showing a schematic configuration of an image flow cytometer 100 according to a first exemplary embodiment.

The attached drawings are for purposes of illustration and are not necessarily to scale.

DETAILED DESCRIPTION

Exemplary embodiments will be described below with reference to the drawings. In the drawings, the same elements are denoted by the same reference numerals, and redundant description is omitted as appropriate.

First Exemplary Embodiment

First, an image flow cytometer 100 according to a first exemplary embodiment will be described. The image flow cytometer 100 can be a scanning-type image flow cytometer. Typical flow cytometers can identify particles or cells based on measurement of detected signals however, correlating those signals to spatial locations on the particles or cells is generally not possible. An "image cytometer" is a cytometer that can provide data relating to a spatial relationship between detected signals and cellular or particle locations. An image cytometer can use an actual imaging camera to create the spatial data, or can use other devices, e.g., as described herein.

FIG. 1 is a configuration diagram showing a schematic configuration of the image flow cytometer 100 according to the first exemplary embodiment. The image flow cytometer 100 includes a flow chamber 1, an irradiation optical system 2, a detection optical system 3, a detection optical system 4, and a control unit 5.

The irradiation optical system 2 radiates laser light L into the flow chamber 1, e.g., to irradiate a microparticulate sample in flow chamber 1. As described in detail later, the irradiation optical system 2 can radiate the laser light L into the flow chamber 1 by causing the laser light L to converge to a diffraction limit. The irradiation optical system 2 can scan the flow chamber 1 with the laser light L. When microparticulate samples flowing through the flow chamber 1 are irradiated with the laser light L, transmitted light/forward-scattered light L_T-FS and fluorescence/side-scattered light L_F-SS can be output from the flow chamber 1. Note that the fluorescence and scattered light can be output in all directions from the flow chamber 1. However, to simplify the explanation in this exemplary embodiment, the fluorescence and side-scattered light which are output in a direction substantially perpendicular to the optical axis of the laser light L are described herein. Light is detected and processed by detection optical system 3 and detection optical system 4. The detection optical systems 3, 4 produce signals SIG_T, SIG_f, respectively, which are provided to a control unit 5. SIG_T or SIG_f can include data for one or more wavelength(s) or component(s) of the light incident on the photodetector 34. The detection optical system 3 is referred to herein, without limitation on angle of placement or orientation, as a parallel detection optical system. This is discussed below with reference to FIG. 17.

The laser light L, or other light radiated into the flow chamber 1, is referred to herein as "incident light." Light transmitted through the flow chamber 1, or light emitted from microparticulate samples, dyes, or other substances within the flow chamber 1, is referred to herein as "resultant light." Resultant light can include forward-scattered (FS) light and side-scattered (SS) light. FS and SS have substantially the same wavelength as the light source. Resultant light can also include fluorescent light, since such light is emitted by substances within the flow chamber 1. Resultant light can be substantially directional (e.g., transmitted light of the laser light L, discussed below with reference to photodetector 34, FIG. 4A) or substantially omnidirectional (e.g., fluorescence).

It is not required that all of the laser light L be incident on the microparticulate sample 61. For example, useful information can be gathered while scanning the irradiation spot over the membrane of a cell, even if some of the irradiation spot is not striking the cell.

In various aspects, light L is provided by a source other than a laser. The light source can be any source that can be focused to produce an irradiation spot smaller than the microparticulate sample to be irradiated, e.g., a lamp positioned at the focus of a parabolic reflector, or a light-emitting diode (LED) focused through a lens.

In an example, the transmitted light/forward-scattered light L_T-FS is coherent light that is affected by scattering, refraction, absorption, rotation of the plane of polarization, or the like of light due to the irradiation of the laser light L onto the microparticulate samples. The fluorescence/side-scattered light L_F-SS is incoherent light. The transmitted light, fluorescence, forward-scattered light, and side-scattered light will be described in detail later. Coherent side-scatter and back-scatter light can also be detected.

In an exemplary aspect, the flow chamber 1 is configured as a flat plate type flow chamber having a micro flow channel through which microparticulate samples to be analyzed flow. The flow chamber 1 is configured such that the microparticulate samples are aligned and permitted to flow through the micro flow channel by hydrodynamic focusing. In other words, in the flow chamber 1, the sample flow is surrounded by a sheath flow including saline, which is an isotonic liquid, and flows through the micro flow channel. In this case, the discharge pressure of the sample flow is set to be higher than that of the sheath flow. This permits the microparticulate samples randomly distributed to be aligned and flow in the sample flow.

Figure 2A:
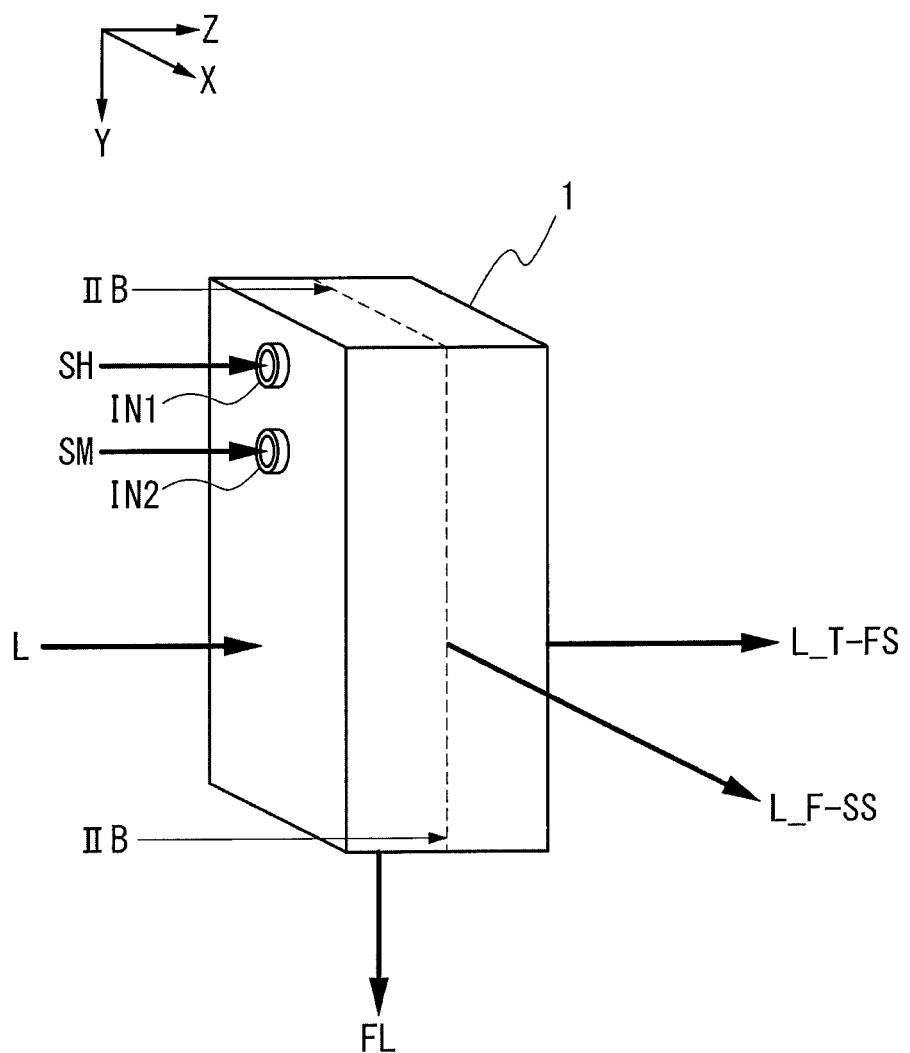
FIG. 2A is a perspective view schematically showing an exemplary configuration of a flow chamber 1.

FIG. 2A is a perspective view schematically showing the configuration of the flow chamber 1. A sheath flow SH flows into the flow chamber 1 from an inlet port IN1. For example, saline, which is an isotonic liquid, can be used as the sheath flow SH. However, the sheath flow SH is not limited to saline, but various types of liquid such as water, other aqueous solutions (whether isotonic or not), and organic solvents can be used.

Further, a sample flow SM including the microparticulate samples flows into the flow chamber 1 from an inlet port IN2. For example, saline, which is an isotonic liquid, can be used as the sample flow SM. However, the sample flow SM is not limited to saline, but various types of liquid such as water, other aqueous solutions (whether isotonic or not), and organic solvents can be used. The inflow pressure of the sample flow SM can be higher than the inflow pressure of the sheath flow SH.

The sheath flow SH and the sample flow SM merge in the flow chamber 1, so that a flow FL in which the sample flow SM is surrounded by the sheath flow SH is generated. The flow FL can be discharged to the outside of the flow chamber 1, for example.

Figure 2B:
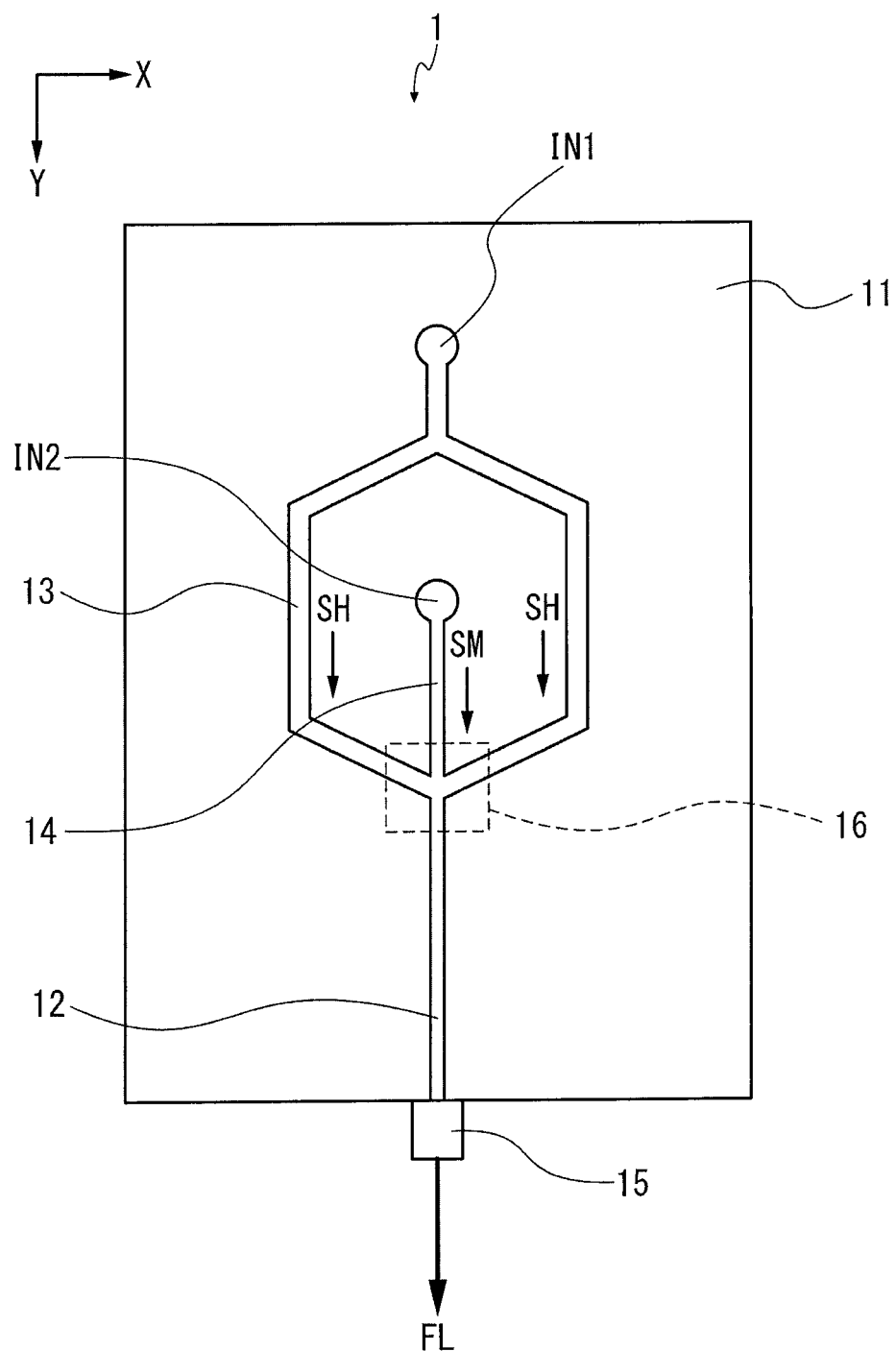
FIG. 2B is a sectional view schematically showing an exemplary sectional configuration of the flow chamber 1 in a plane taken along the line IIB-IIB of FIG. 2A.

FIG. 2B is a sectional view schematically showing a sectional configuration of the flow chamber 1 in a plane taken along the line IIB-IIB of FIG. 2A according to various aspects. Note that in FIG. 2B, a direction which is perpendicular to a Y-direction and parallel to the plane of the drawing is an X-direction. In the flow chamber 1, a micro flow channel 12, a flow channel 13, and a flow channel 14 are formed in a flat-plate-shaped member 11 through which laser light can be transmitted. The flow channel 13 is connected to the inlet port IN1 which is a pipe line that is bored in the surface of the flow chamber 1. Accordingly, the sheath flow SH flows through the flow channel 13. The flow channel 13 is branched into two channels, for example. The flow channel 14 is connected to the inlet port IN2 which is a pipe line that is, e.g., bored in the surface of the flow chamber 1. Accordingly, the sample flow SM flows through the flow channel 14. The flow channel 14 and the branched flow channels 13 merge and are connected with the micro flow channel 12. The micro flow channel 12 is a micro flow channel through which the microparticulate samples to be analyzed pass. The laser light L from the irradiation optical system 2 is radiated onto the micro flow channel 12 in the direction from the front side of the plane of FIG. 2B toward the back side thereof, that is, in the direction perpendicular to the Y-direction. The orientations of components shown in this example are not limiting.

Figure 2C:
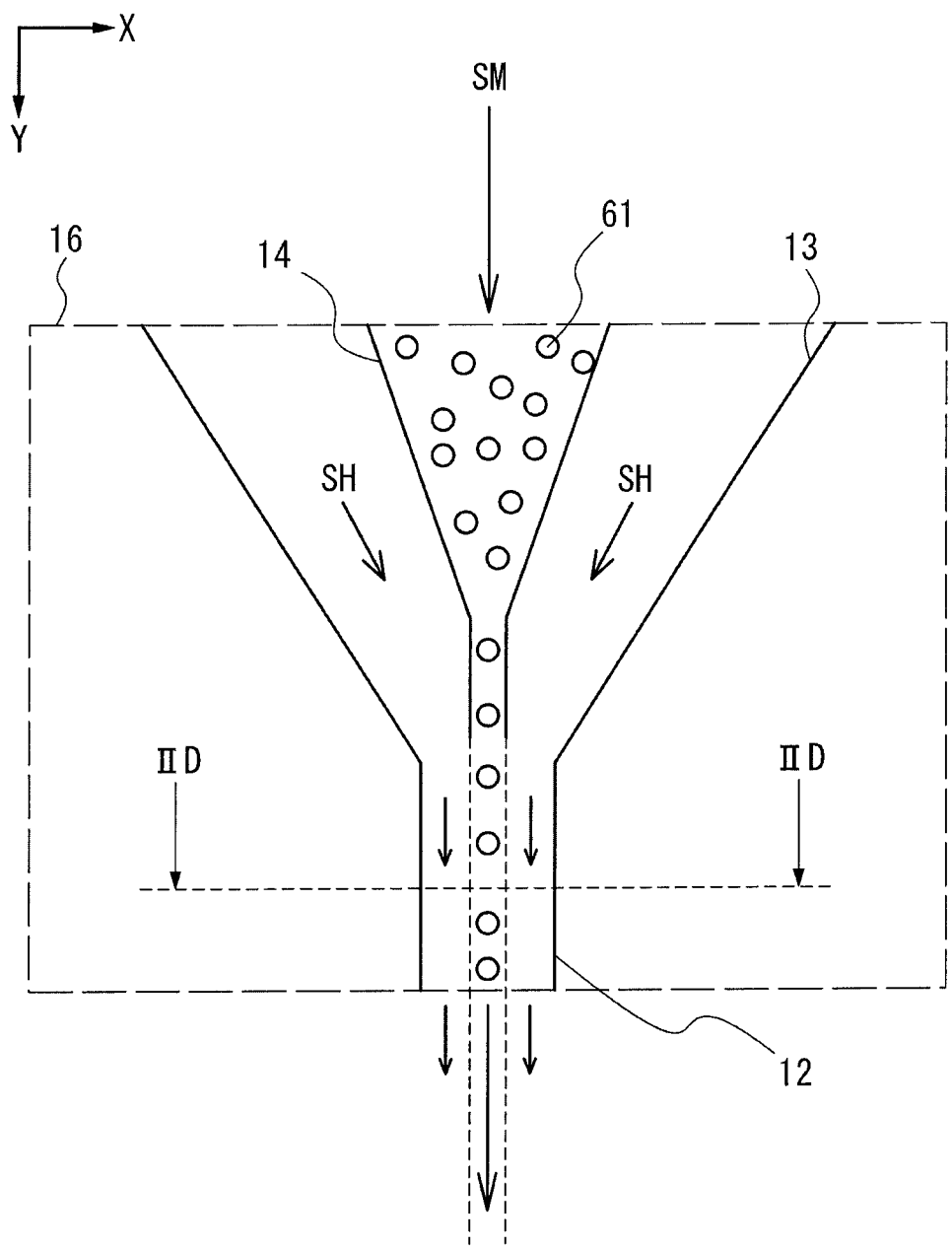
FIG. 2C is an enlarged sectional view schematically showing an exemplary confluent portion 16 shown in FIG. 2B.

FIG. 2C is an enlarged sectional view schematically showing a confluent portion 16 shown in FIG. 2B according to various aspects. The sheath flow SH merges with the sample flow SM so as to enclose the sample flow SM. In this case, since the inflow pressure of the sample flow SM is higher than the inflow pressure of the sheath flow SH, microparticulate samples 61, which are randomly distributed, are aligned and flow in the sample flow SM within the micro flow channel 12.

Figure 2D:
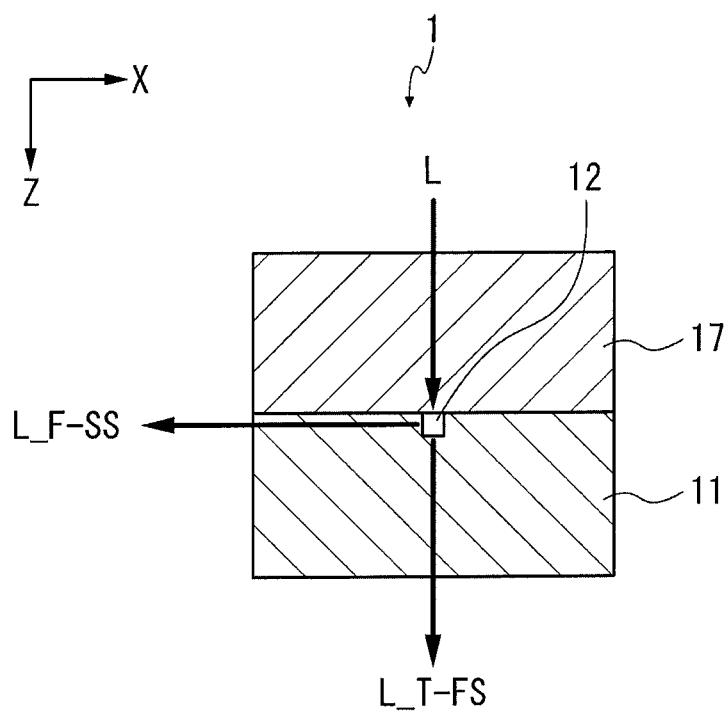
FIG. 2D is a sectional view schematically showing an exemplary sectional configuration of the flow chamber 1 taken along the line IID-IID of FIG. 2C.

FIG. 2D is a sectional view schematically showing a sectional configuration of the flow chamber 1 taken along the line IID-IID of FIG. 2C according to various aspects. The micro flow channel 12 is formed as a groove in the flat-plate-shaped member 11. The flat-plate-shaped member 11 and the micro flow channel 12 are covered with a flat-plate-shaped member 17 through which laser light can be transmitted. In FIG. 2B, the laser light L from the irradiation optical system 2 is incident on the upper surface of the flow chamber 1 from a Z-direction, which is a direction perpendicular to each of the X-direction and the Y-direction. The thickness in the Z-direction of each of the flat-plate-shaped member 11 and the flat-plate-shaped member 17 is 1 mm, for example. The flat-plate-shaped member 11 and the flat-plate-shaped member 17 are formed of a light transmissive material, such as resin, glass, or quartz, through which the laser light L can be transmitted.

In the flow cytometry, microparticulate samples to be analyzed are often cells of a living organism. Taking human blood as an example, examples of objects to be observed in the blood include erythrocytes (diameter of 7 to 8 μm, thickness of about 2 μm), leucocytes (neutrophils: diameter of 12 to 15 μM, acidocytes: diameter of 10 to 15 μm, basophils: diameter of 10 to 15 μm, lymphocytes: diameter of 6 to 15 μm, monocytes: diameter of 20 to 30 μm), and blood platelets (diameter of 1 to 4 μm). The micro flow channel 12 is formed with dimensions that permit the microparticulate samples to be aligned in the Y-direction and move without overlapping each other within the flow channel. The micro flow channel 12 has a section size of the square of 50 μm, for example, in the configuration shown in FIG. 2B.

Figure 2E:
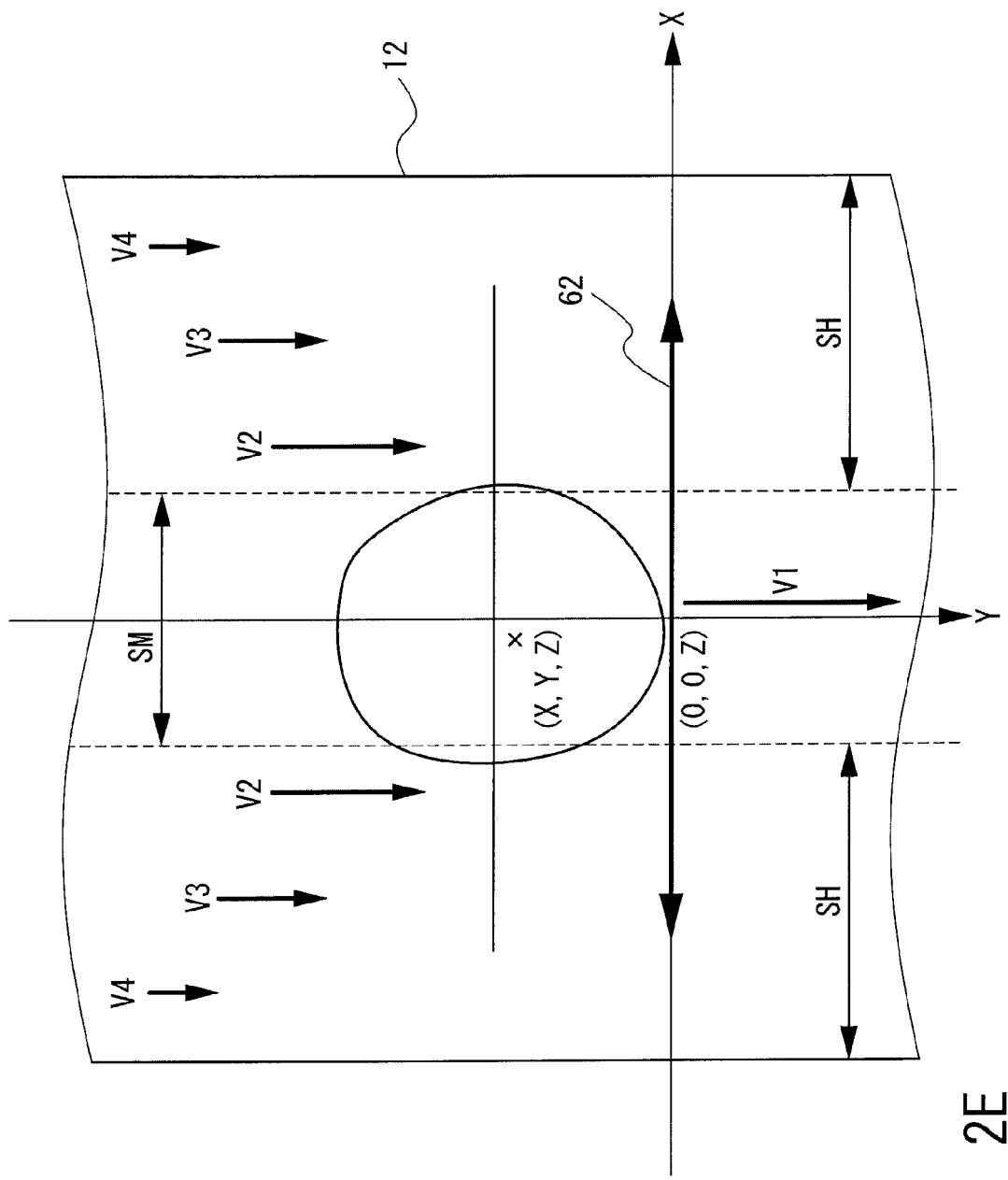
FIG. 2E is an enlarged front view showing a substantial part of a micro flow channel 12 according to various aspects.
Figure 2F:
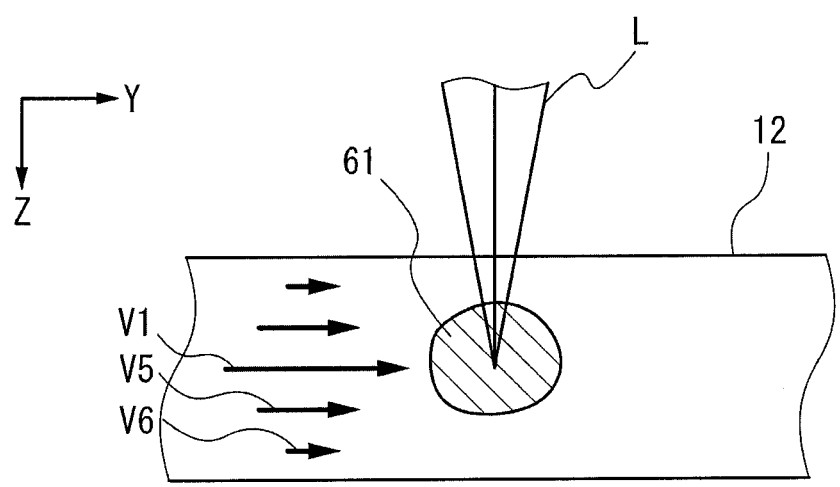
FIG. 2F is an enlarged sectional view showing the substantial part of the micro flow channel 12 in an exemplary Y-Z section of FIG. 2E.

FIG. 2E is an enlarged front view showing a substantial part of the micro flow channel 12 according to various aspects. FIG. 2F is an enlarged sectional view showing the substantial part of the micro flow channel 12 in a Y-Z section of FIG. 2E. The flow rate of the liquid within the micro flow channel 12 shows such a parabolic change that the sample flow SM positioned at the center of the section (a flow rate V1 in FIGS. 2E and 2F) is fastest and the sheath flow SH becomes slower toward the wall surface of the micro flow channel 12 (V2 to V4 (V1>V2>V3>V4) in FIG. 2E) and V5 and V6 (V1>V5>V6) in FIG. 2F). As a result, the microparticulate samples 61 which move within the micro flow channel 12 move in the vicinity of the center of the section of the micro flow channel 12 so that the center-of-gravity position (X,Y,Z) is positioned substantially within the sample flow SM. Accordingly, even when the section size of the micro flow channel 12 is larger than that of each microparticulate sample 61, the plurality of microparticulate samples 61 can be aligned an move in a flow direction (Y-direction in FIGS. 2C and 2D) without overlapping with each other in the section of the micro flow channel 12.

Referring to FIGS. 2E and 2F, as shown, the irradiation optical system 2 (FIG. 1) irradiates the microparticulate sample 61 (or other object) in the micro flow channel 12 with incident light L in an irradiation spot smaller than the microparticulate sample 61. As discussed below with reference to FIG. 3A, the irradiation optical system 2 scans an irradiation position of the irradiation spot substantially in a direction X perpendicular to the flow direction Y. In doing so, the irradiation optical system 2 scans the irradiation position through an irradiation volume, e.g., a volume the size of the irradiation spot swept along the path 62 shown in FIG. 2E. In various aspects, the micro flow channel 12 is shaped so that only one of the microparticulate sample 61 can be in the irradiation volume at one time. This advantageously provides measurement of the microparticulate sample 61 without concern for "coincidences," events in which two microparticulate samples 61 are erroneously detected as one microparticulate sample 61.

Figure 3A:
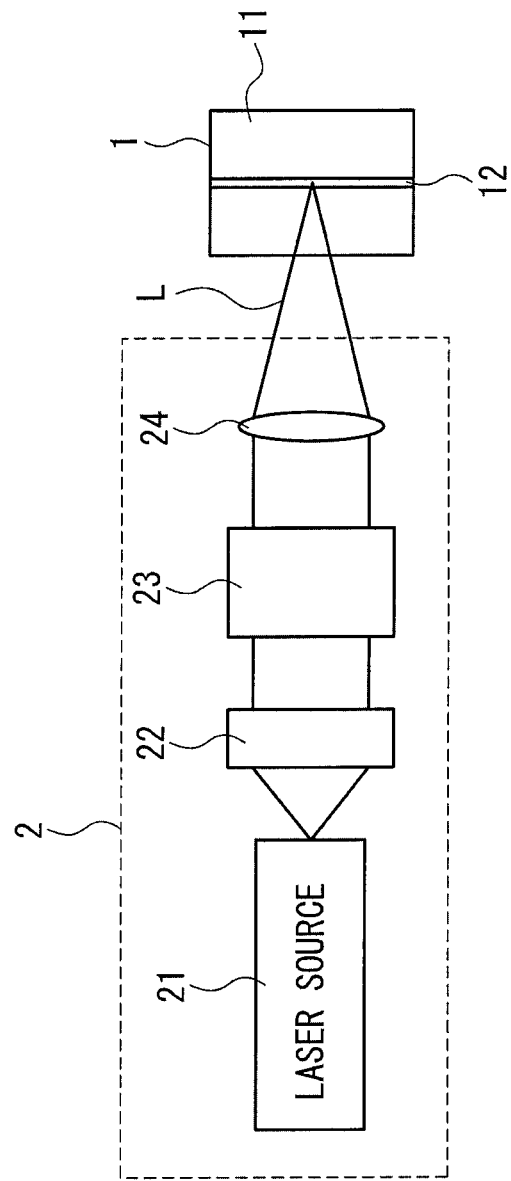
FIG. 3A is a block diagram schematically showing an exemplary configuration of an irradiation optical system 2.

The irradiation optical system 2 will now be described. FIG. 3A is a block diagram schematically showing the configuration of the irradiation optical system 2 according to various aspects. The irradiation optical system 2 includes a laser source 21, a collimator 22, a deflector 23, and an objective lens 24. The laser source 21 can produce laser light having wavelengths of 405 nm, 488 nm, and 650 nm, for example. However, the light wavelengths are not limited to these examples. The laser light L output from the laser source 21 is converted into substantially parallel light beams by the collimator 22. Note that the micro flow channel 12 is shown on the plane of FIG. 3A for convenience of explanation, but in various aspects, the upper surface in which the micro flow channel 12 of the flow chamber 1 is formed faces the left side of the plane of FIG. 3A. In an example, astigmatic focusing is used to focus the laser light L on the micro flow channel 12.

The deflector 23 is a light deflector that deflects the direction of the optical axis of the laser light L passing through the collimator 22. In this exemplary embodiment, the deflector 23 is configured to be able to scan the laser light L in a direction substantially parallel to the section of the micro flow channel 12 of the flow chamber 1 (that is, in the X-direction orthogonal to the flow direction of the micro flow channel 12). In this case, the deflector 23 scans the micro flow channel 12 in the X-direction (a path 62 shown in FIG. 2E) with a scanning frequency of 1 MHz or higher. To achieve such high-speed scanning, a high-frequency deflection device such as an acoustic optical deflector (AOD), an electro-optic deflector (EOD), or acoustic optic modulator (AOM) can be used as the deflector 23. AODs, EODs, and AOMs make use of the interaction of light with materials whose interaction with electromagnetic radiation can be modified by applied force (AODs or AOMs) or electric field (EODs). The incident light can also be scanned using a rotating polygon such as those used in laser electrophotographic printers. The incident light can also be scanned using a microelectromechanical system (MEMS) micro-mirror with an electronically-controllable angle.

As shown in FIG. 3A, the laser light L passing through the deflector 23 is caused to converge, e.g., at the diffraction limit, on the micro flow channel 12 of the flow chamber 1 by the objective lens 24. In an example, the laser light is caused to converge to a laser spot with a half-value breadth of about 2.0μm. Hereinafter, the size of the laser irradiation spot is defined as an area from the center of the spot to the position where the light intensity is a half of that at the center of the spot. The microparticulate samples are self-aligned in the vicinity of the center of the micro flow channel due to the properties of the micro flow channel described above. Therefore, the focal point of the laser light is configured such that the path to be scanned by the irradiation spot passes through the center of the micro flow channel, which facilitates irradiation of the laser light that is caused to converge, e.g., at the diffraction limit, on the microparticulate samples flowing through the micro flow channel. Note that in this example, the deflection angle of the laser light L by the deflector 23 is small. Accordingly, even when the laser light L is incident through the flat-plate-shaped member 17 of the flow chamber 1, effects such as a displacement of the focal point position due to refraction are negligibly small.

Figure 3B:
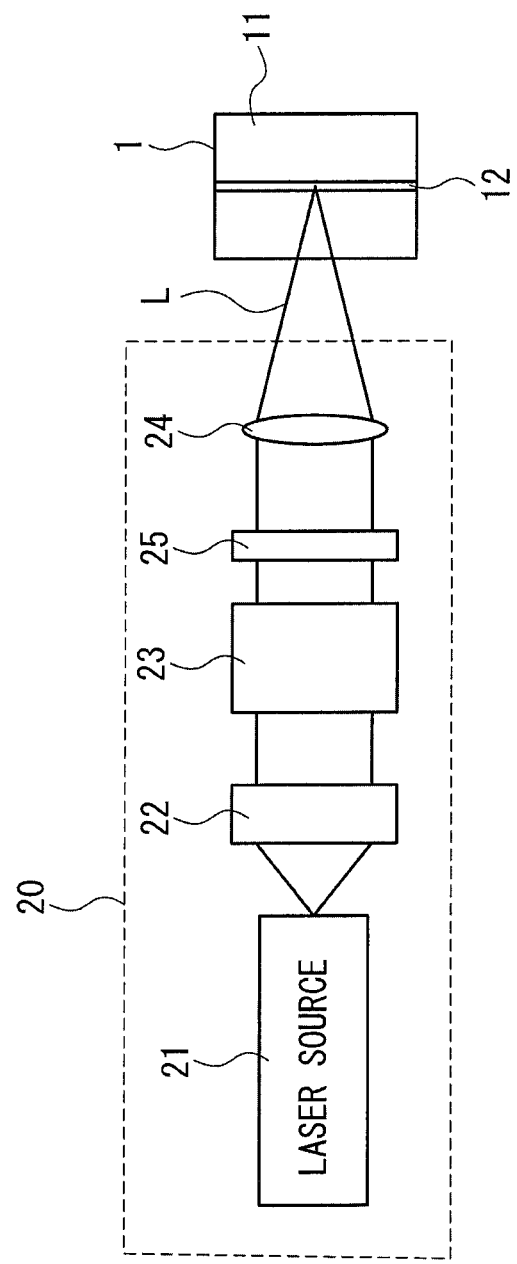
FIG. 3B is a block diagram schematically showing an exemplary irradiation optical system 20 that is another configuration of the irradiation optical system 2.
Figure 4A:
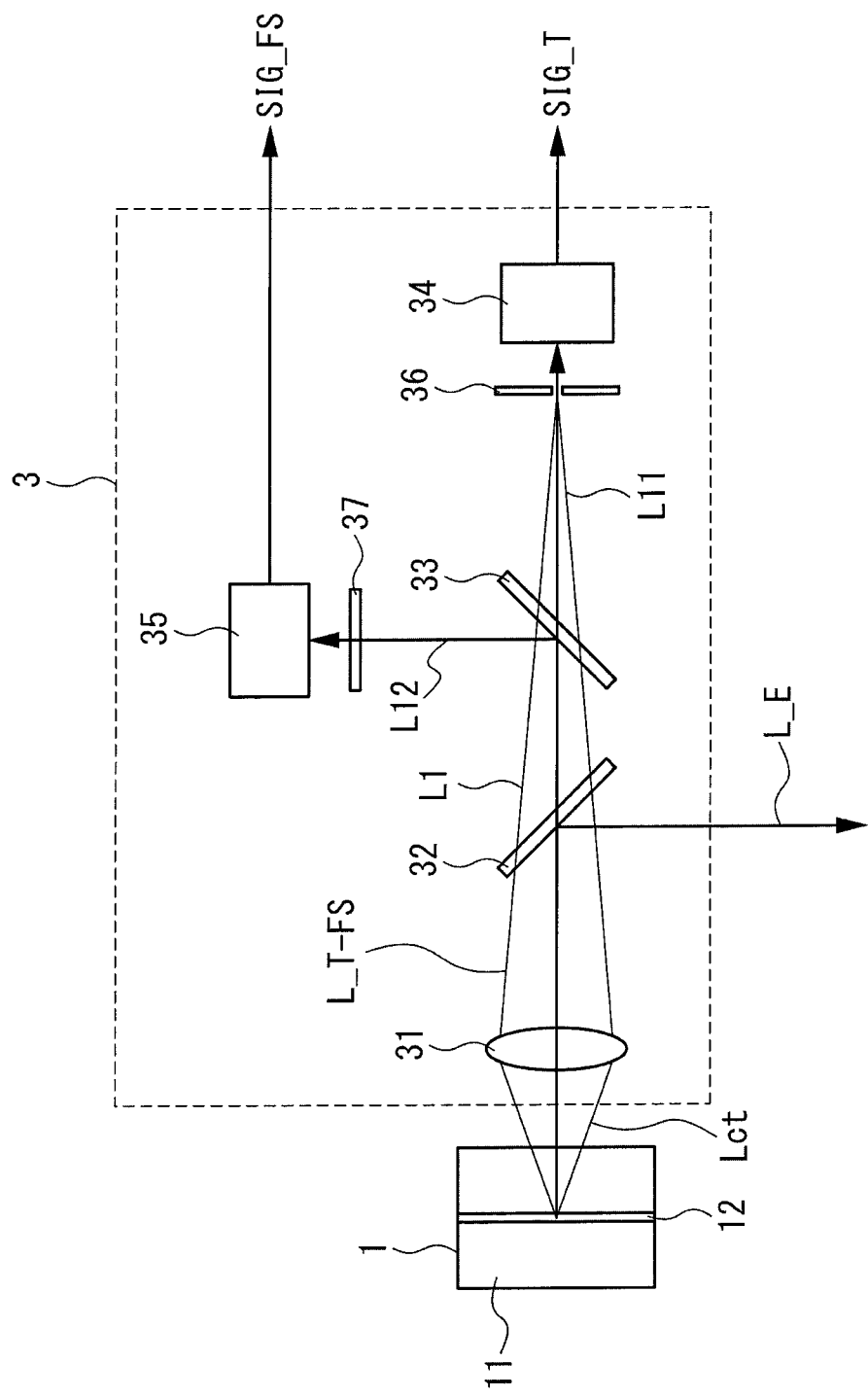
FIG. 4A is a configuration diagram schematically showing an exemplary configuration of a detection optical system 3.
Figure 4B:
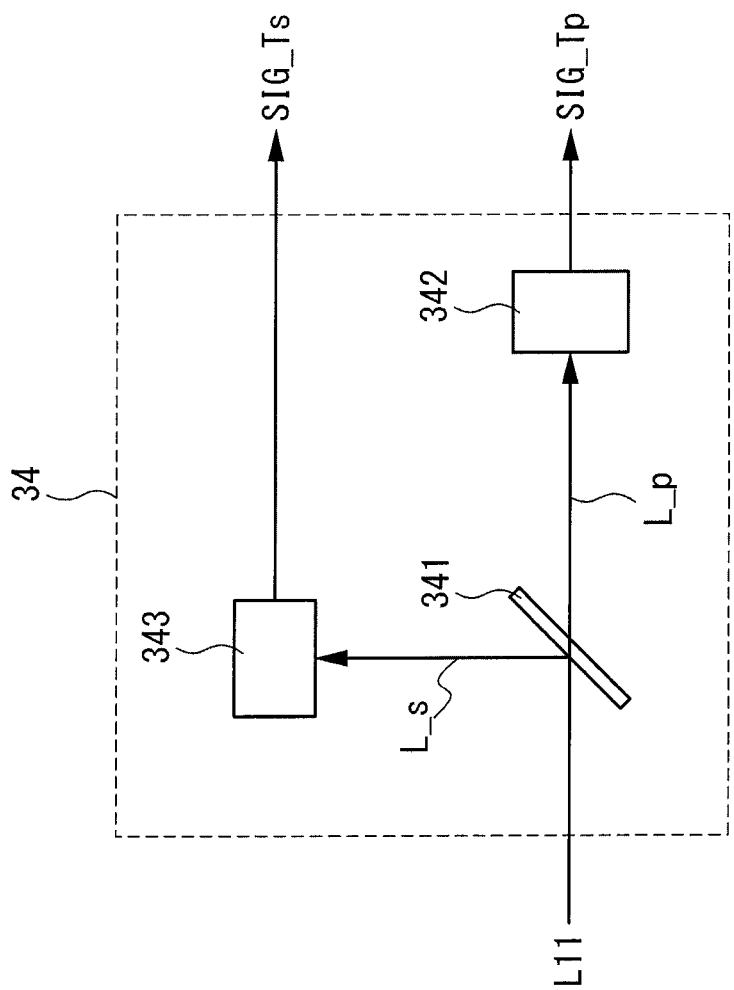
FIG. 4B is a configuration diagram showing an example of the configuration of the photodetector 34 of the detection optical system 3.

FIG. 3B is a block diagram schematically showing an irradiation optical system 20 that is another configuration of the irradiation optical system 2. The irradiation optical system 20 has a configuration in which a $\lambda/4$ plate 25 is added to the irradiation optical system 2 shown in FIG. 3A. $\lambda$ is the wavelength of the light from the laser source 21. The $\lambda/4$ plate 25 is placed in the light path of the laser light L. For example, the $\lambda/4$ plate 25 is interposed between the deflector 23 and the objective lens 24. The $\lambda/4$ plate 25 converts a linear polarized light into a circular polarized light. Other optical structures for providing circularly-polarized light can also be used. Live cells or proteins generally show polarization characteristics. Therefore, polarization microscopes can be useful for biological observation. In order detect polarization characteristics of a material in a microparticulate sample, the incident light beam is preferably symmetric for all directions. Circularly-polarized beams advantageously exhibit this property. However, many AODs and EODs operate with linear polarization of the incident beam, typically perpendicular polarization. Inserting a quarter wave plate to convert from linear to circular polarization permits using an AOD or EOD and preserving the desirable biological properties of circularly-polarized light. As discussed below with reference to FIG. 6, detecting p and s polarization components permits determining polarization characteristics of microparticulate samples. FIGS. 4A and 4B show an example of a detection optical system that can be designed to detect polarization components.

Returning to FIG. 1, the configuration of the image flow cytometer 100 will be further described. The detection optical system 3 is disposed at a position opposed to the irradiation optical system 2 through the flow chamber 1. The detection optical system 3 detects the transmitted light of the laser light irradiated onto the micro flow channel 12, and also detects the forward-scattered light generated by the irradiation of the microparticulate samples by the laser light. The term "forward-scattered light" refers to light that is scattered at a small angle with respect to the traveling direction of the optical axis of the laser light L. This forward-scattered light can include scattered light generated when the laser light is scattered on the surface of each microparticulate sample, or diffracted light or refracted light that are generated when the laser light is radiated onto each microparticulate sample. In an example, when the microparticulate samples to be irradiated with the laser light are cells, the forward-scattered light varies depending on, e.g., the state of a cell surface, the shape and the presence or absence of a nucleus, the shape of each cell, or a direction in which laser light passes through each cell.

FIG. 4A is a configuration diagram schematically showing an exemplary configuration of the detection optical system 3, e.g., for detecting transmitted or forward-scattered light. The detection optical system 3 includes an objective lens 31, a dichroic mirror 32, a beamsplitter 33 (e.g., a half-silvered mirror), photodetectors 34 and 35, a confocal aperture 36, and a block filter 37. First, light Lct from the flow chamber 1 falls on the objective lens 31. The objective lens 31 causes the incident light to form an image on the receiving surface of the photodetector 34. The dichroic mirror 32 reflects light L_E having wavelengths other than a wavelength $\lambda L$, which is the wavelength of the laser light, out of the transmitted light/forward-scattered light L_T-FS. This permits extra components such as the fluorescence to be partly or wholly removed from the transmitted light/forward-scattered light L_T-FS, and permits light L1 having substantially the same wavelength $\lambda L$ as that of the laser light to be output from the dichroic mirror 32. In an example, only light L1 is output from the dichroic mirror 32. The light L1 is split into light L11 and light L12 by the beamsplitter 33. A metal half-silvered mirror can be used; such beamsplitters have a wide spectrum but large absorption. A multi-layer dielectric beam splitter can also be used. Such dielectric beamsplitters can have lower absorption than metal half-silvered mirrors.

The confocal aperture 36 is a pin-hole, for example, and removes the forward-scattered light having at least a selected angle with respect to the optical axis of the laser light L from the light L11. This permits the transmitted light included in the light L11 to be incident on the photodetector 34. In an example, only the transmitted light in L11 is incident on photodetector 34. The photodetector 34 detects the light intensity of the transmitted light, and outputs the detection result as a detection signal SIG_T.

Light L12 is a portion of light L1. The block filter 37 removes, from the light L12, the transmitted light that propagates along the optical axis of the light L12. The block filter 37 can include, e.g., a slit structure. The block filter can collect a limited-scatter-angle component, e.g., in the 1-10° range. This permits the forward-scattered light to be incident on the photodetector 35, but not the transmitted light (any extra components were already removed by dichroic mirror 32). The photodetector 35 detects the light intensity of the forward-scattered light included in the light L12, and outputs the detection result as a detection signal SIG_FS.

FIG. 4B is a configuration diagram showing an example of the configuration of the photodetector 34 of the detection optical system 3. The photodetector 34 is used with the irradiation optical system 20 described above. The photodetector 34 includes a polarizing beam splitter 341, an s-polarized light detector 343, and a p-polarized light detector 342. The light L11 passing through the confocal aperture 36 is incident on the polarizing beam splitter 341. An s-polarized light L_s included in the light L11 is reflected by the polarizing beam splitter 341, and a p-polarized light L_p included in the light L11 is transmitted through the polarizing beam splitter 341. The s-polarized light detector 343 detects the intensity of the s-polarized light L_s and outputs a detection signal SIG_Ts as a detection result. The p-polarized light detector 342 detects the intensity of the p-polarized light L_p and outputs a detection signal SIG_Tp as a detection result. The detection signals SIG_Ts and SIG_Tp are parts of the detection signal SIG_T shown in FIG. 4A.

Returning to FIG. 1, the configuration of the image flow cytometer 100 will be further described. The detection optical system 4 is disposed at a position deviating from the optical axis of the laser light L. For example, the detection optical system 4 is disposed in a direction substantially perpendicular to the optical axis of the laser light L, or at least 45° away from the optical axis of laser light L. Accordingly, the fluorescence that propagates in the direction perpendicular to the optical axis of the laser light L is incident on the detection optical system 4. The term "side-scattered light" refers to light that is scattered in a direction substantially perpendicular (about 90°) to the optical axis of the laser light. In general, the side-scattered light has a light intensity smaller than that of the forward-scattered light. In an example, the microparticulate samples to be irradiated with the laser light are cells, and the side-scattered light is produced due to an internal structure of each cell such as intracellular granules or a nucleus.

Figure 5:
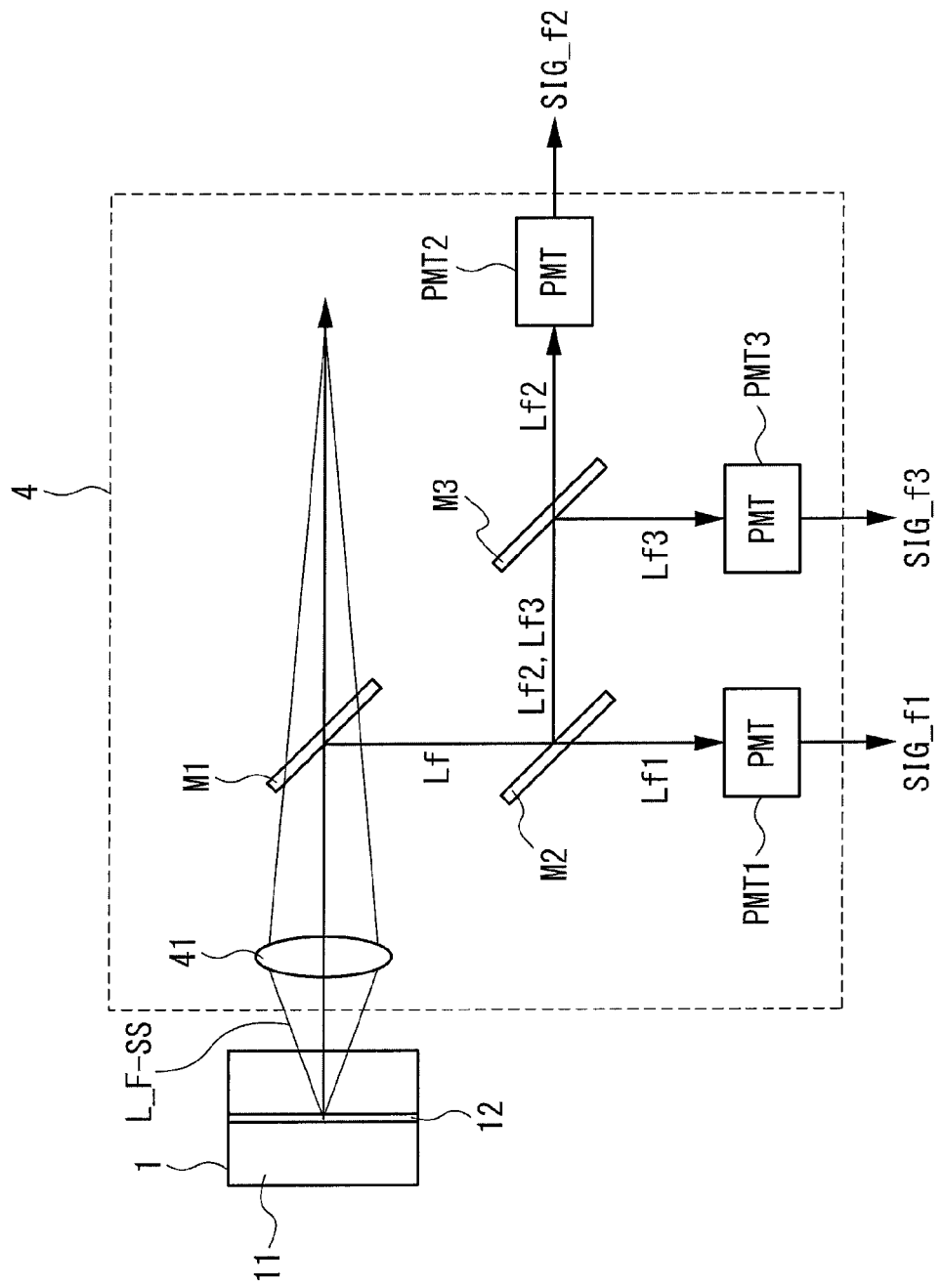
FIG. 5 is a configuration diagram schematically showing an exemplary configuration of a detection optical system 4.

FIG. 5 is a configuration diagram schematically showing an exemplary configuration of the detection optical system 4. The detection optical system 4 includes objective lens 41, dichroic mirrors M1, M2, and M3 and photomultiplier tubes (PMTS) PMT1, PMT2, and PMT3. First, the fluorescence/side-scattered light L_F-SS from the flow chamber 1 passes through the objective lens 41. The objective lens 41 causes the incident light to form an image a selected focal distance beyond the objective lens 41. The light from the objective lens 41 is incident on the dichroic minor M1. The dichroic mirror M1 reflects light having wavelengths other than the wavelength λL, which is the same wavelength as that of the laser light, out of the fluorescence/side-scattered light L_F-SS. This permits fluorescence Lf (or other extra components not at wavelength λL) to be incident on the dichroic minor M2. Lf is obtained by removing the side-scattered light having the same wavelength as that of the laser light from the fluorescence/side-scattered light L_F-SS. In an example, the fluorescence Lf includes fluorescences having three wavelengths λ1, λ2, λ3 (λ1<λ2<λ3). As for the fluorescence Lf, the dichroic mirror M2 permits only fluorescence light Lf1 having the wavelength λ1 to be transmitted and reflects fluorescence light Lf2 having the wavelength λ2 and a fluorescence Lf3 having the wavelength λ3. After that, the fluorescence light Lf2 having the wavelength λ2 is transmitted through the dichroic mirror M3, and the fluorescence light Lf3 having the wavelength λ3 is reflected by the dichroic minor M3.

The photomultiplier tube PMT1 detects the light intensity of the fluorescence light Lf1, which has the wavelength λ1 and has been transmitted through the dichroic minor M2, and outputs the detection result as a detection signal SIG_f1. The photomultiplier tube PMT2 detects the light intensity of the fluorescence light Lf2, which has the wavelength λ2 and has been transmitted through the dichroic mirror M3, and outputs the detection result as a detection signal SIG_f2. The photomultiplier tube PMT3 detects the light intensity of the fluorescence light Lf3, which has the wavelength λ3 and has been reflected by the dichroic minor M3, and outputs the detection result as a detection signal SIG_f3. Note that the detection signal SIG_f1 to SIG_f3 are parts of SIG_f in FIG. 1.

Referring back to FIG. 1, the control unit 5 is configured as a hardware resource, such as a computer, which is capable of executing information processing, for example. The control unit 5 performs arithmetic processing based on the detection signals SIG_T and SIG_FS from the detection optical system 3 and the detection signals SIG_f1 to SIG_f3 from the detection optical system 4. The control unit 5 can also control the rate and cycle of the deflection operation for the laser light L in the deflector 23. Other examples of hardware and software that can be included in the control unit 5 are discussed below with reference to FIG. 18.

Figure 6:
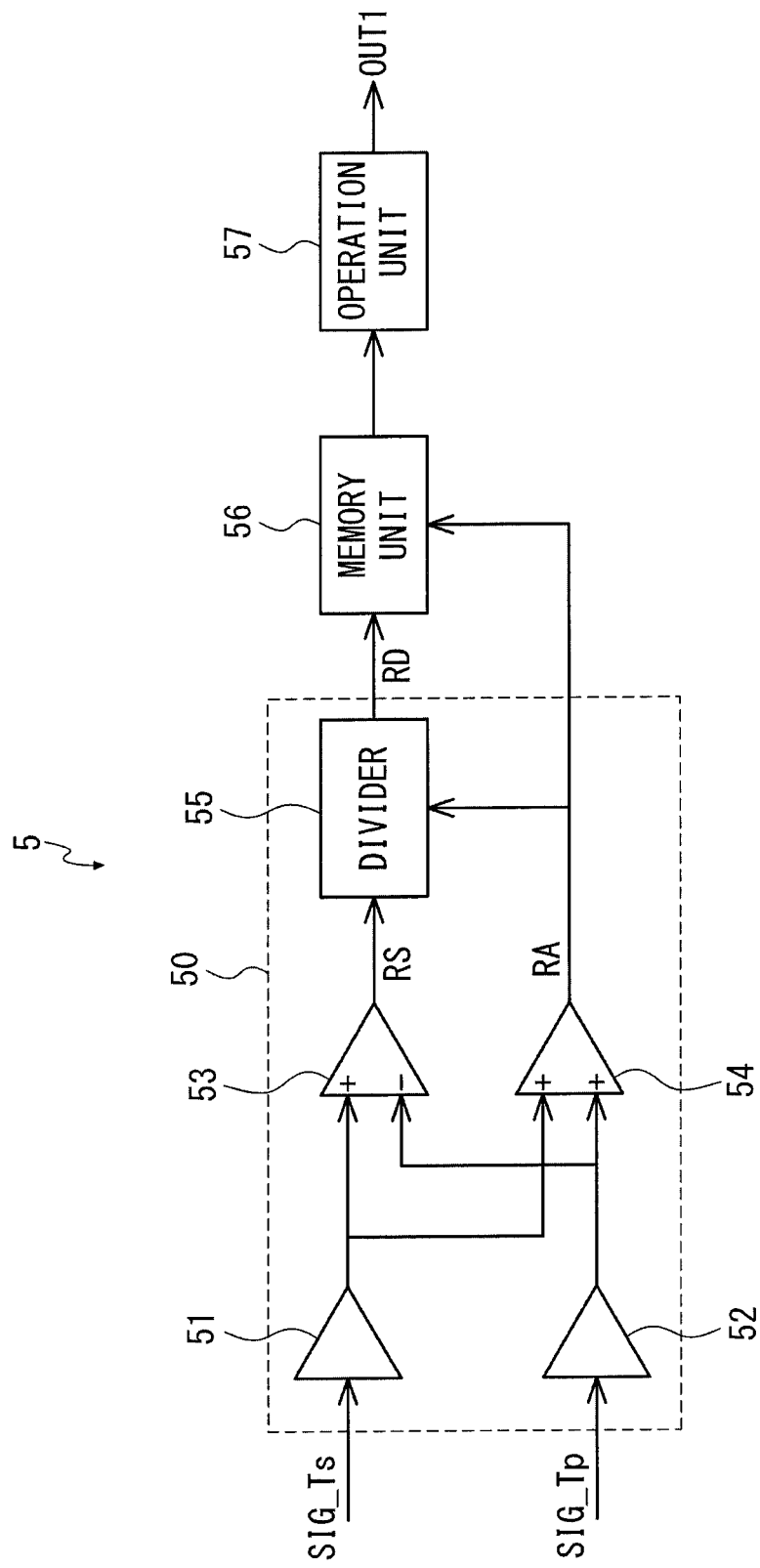
FIG. 6 is a block diagram showing an exemplary configuration of the control unit 5.

An example of the configuration of the control unit 5 is described. FIG. 6 is a block diagram showing the example of the configuration of the control unit 5. The control unit 5 includes a signal processing unit 50, a memory unit 56, and an operation unit 57. The signal processing unit 50 includes amplifiers 51 and 52, a subtractor 53, an adder 54, and a divider 55. The detection signals SIG_Ts and SIG_Tp output from the photodetector 34 shown in FIG. 4B is input to the signal processing unit 50.

The amplifier 51 amplifies the detection signals SIG_Ts and outputs the amplified detection signals SIG_Ts to the subtractor 53 and adder 54. The amplifier 52 amplifies the detection signals SIG_Tp and outputs the amplified detection signals SIG_Tp to the subtractor 53 and adder 54. Amplifiers 51, 52 can be unity-gain amplifiers, i.e., buffers (analog or digital). The subtractor 53 subtracts the detection signals SIG_Tp from the detection signals SIG_Ts and outputs a subtraction result RS to the divider 55. Note that the subtractor 53 can subtract the detection signals SIG_Ts from the detection signals SIG_Tp and outputs a subtraction result RS to the divider 55. The adder 54 adds the detection signals SIG_Tp to the detection signals SIG_Ts and outputs an addition result RA to the divider 55. Further, the adder 54 writes the addition result RA into the memory unit 56. The divider 55 divides the subtraction result RS by the addition result RA and writes a division result RD into the memory unit 56: for example, $$RD = \frac{SIG\_Ts - SIG\_Tp}{SIG\_Ts + SIG\_Tp}. \quad (1)$$

The division result RD can represent an unbalance of polarization of the transmitted light.

The operation unit 57 retrieves the addition result RA and the division result RD from the memory unit 56. The operation unit 57 can output a two-dimensional distribution (e.g., a two-dimensional image) of the transmitted light intensity OUT1 using the addition result RA representing the transmitted light intensity. The two-dimensional distribution relates to the scanning pattern of the irradiation spot, e.g., as discussed below with reference to FIG. 8A. Note that the division result RD represents an unbalance of polarization of the transmitted light. Thus, the operation unit 57 can indicate the unbalance of polarization on the two-dimensional image representing two-dimensional distribution of the transmitted light by coloring or the like. Therefore, it is possible to observe not only the shape of the microparticulate sample but also the inner structure of the microparticulate sample that is a cause of the polarization. Cell polarization images can be used to analyze live cells without requiring fluorescence or fluorescent dyes. Cell division can also be observed by polarization observation. Polarized light can also be used for measuring the lipid structure of membranes (e.g., lipid bilayers). For example, cell rigidity can be measured using two polarized (vertical and horizontal) signals. The rigidity of the cell is correlated with cell age, and can also indicate activation state. Organized structures (e.g., actin or collagen) show highly directional responses when using polarized light.

Figure 7:
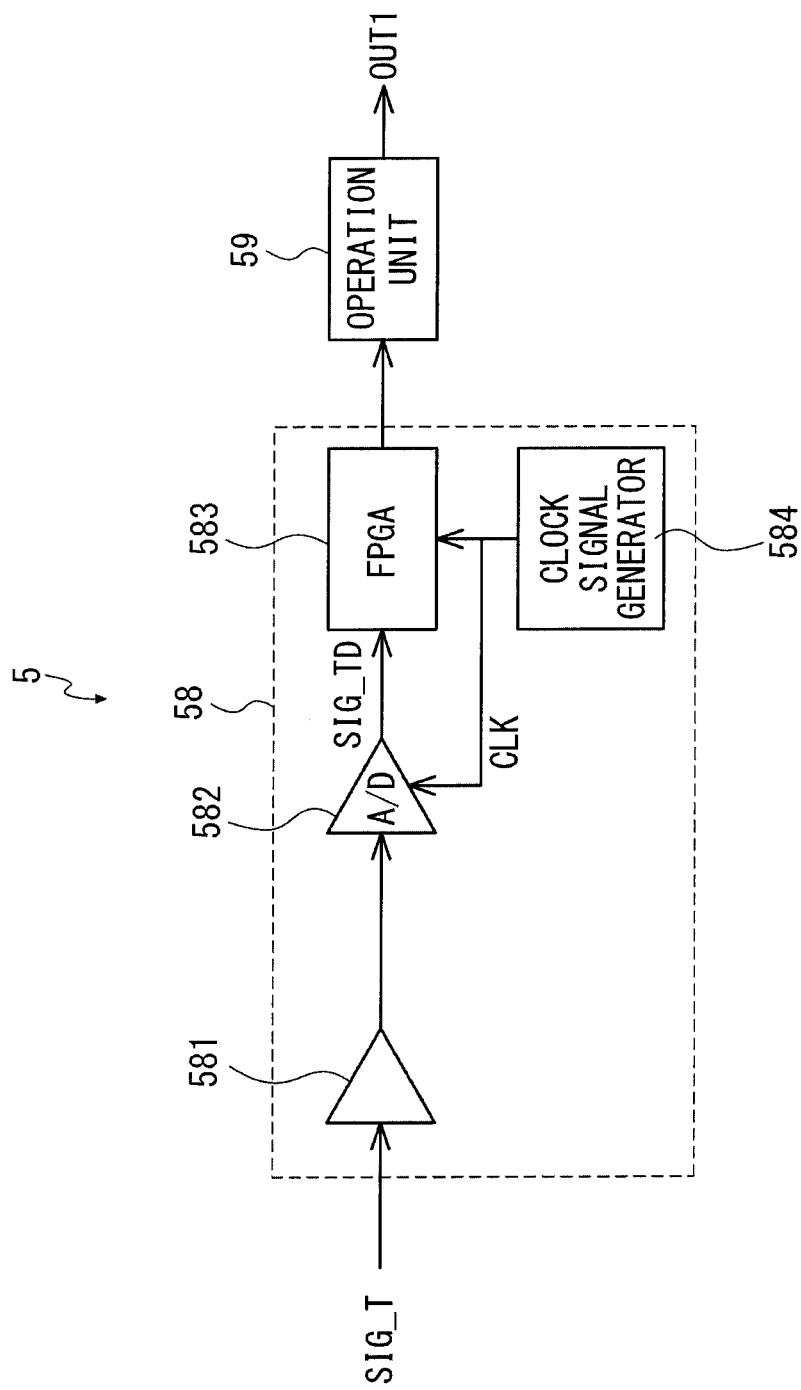
FIG. 7 is a block diagram showing another exemplary configuration of the control unit 5.

Subsequently, another example of the configuration of the control unit 5 is described. FIG. 7 is a block diagram showing the another example of the configuration of the control unit 5. The control unit 5 shown in FIG. 7 is a formed as a circuit performing digital signal processing. The control unit 5 shown in FIG. 7 includes a signal processing unit 58 and an operation unit 59. The signal processing unit 58 can correspond to the signal processing unit 50 shown in FIG. 6. The signal processing unit 58 includes an amplifier 581, an analog to digital (A/D) converter 582, a field-programmable gate array (FPGA) 583, and a clock signal generator 584.

The amplifier 581 (which can be a unity-gain buffer) amplifies the detection signal SIG_T and provides the amplified detection signal SIG_T to the A/D converter 582. The A/D converter 582 converts the detection signal SIG_T which is an analog signal into a digital signal SIG_TD. The FPGA 583 performs the digital signal processing using the digital signal SIG_TD in synchronization with a clock signal from the clock signal generator 584, and outputs a signal representing the transmitted light intensity to the operation unit. The operation unit 59, which is an image processor, for example, outputs the two-dimensional image representing two-dimensional distribution of the transmitted light using the signal output from the FPGA 583. Note that the control unit 5 shown in FIG. 7 can perform the same operation as the control unit 5 shown in FIG. 6 when the detection signals SIG_Tp to the detection signals SIG_Ts are parts of the detection signal SIG_T.

Figure 8A:
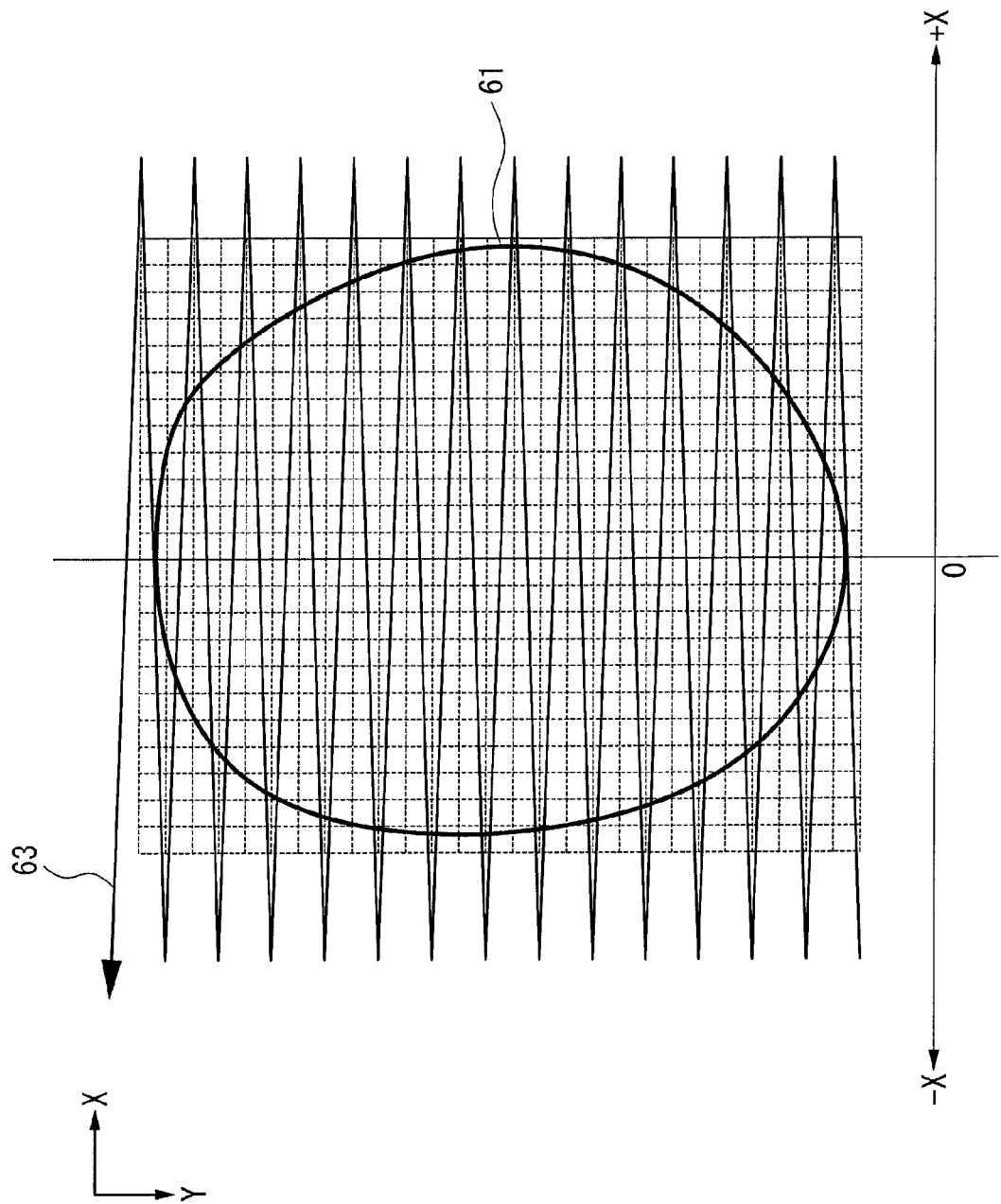
FIG. 8A is a to view showing a substantial part of a microparticulate sample 61 flowing through the micro flow channel 12.

Subsequently, the detection operation in the image flow cytometer 100 will be described. FIG. 8A is an exemplary front view of a substantial part of the microparticulate sample 61 flowing through the micro flow channel 12. In this exemplary embodiment, the microparticulate samples flow at a certain rate within the micro flow channel 12. In this exemplary embodiment, the flow rate of the microparticulate samples is 1 m/s. The flow rate of 1 m/s is substantially equal to a typical flow rate of blood in blood vessels (excluding peripheral capillaries) of a human body. Accordingly, when human blood cells are used as the microparticulate samples, the cells can be observed in the same state as in blood vessels.

In various aspects, the flow velocity, spot size, and X-axis deflection frequency parameters are set to (1) provide an excitation intensity level of a fluorescent dye marker in a desired area of the microparticulate sample above a threshold; and (2) provide a desired resolution, bit depth, and precision of the scan image. In various aspects, the spot size is selected, then flow velocity and scan frequency are controlled. An example is a spot with a full width at half maximum (FWHM) of 2μm (e.g., as discussed above with reference to the "half-value breadth"), a deflection frequency of 1MHz, and a flow rate of 1m/s. This example provides 1 μm scan vertical resolution with >1/2 intensity of a Gaussian spot profile. A 2μm FWHM advantageously permits measuring data from 10μm particles such as blood cells with effective focal depth. In another example, the spot size is 0.5μm, which provides higher resolution-. The flow speed can be 1/4 m/s, or the scan frequency can be 4MHz, or a combination. Generally, flow speed can be reduced or scan frequency can be increased by the same ratio as the spot size is decreased, or vice versa (increase spot size and increase flow speed or decrease scan frequency). Flow speed can be selected to balance desired resolution and throughput. Faster flow speed provides higher throughput and lower vertical resolution. Slower flow speed improves vertical image resolution with lower throughput. The horizontal resolution is determined by the scanning frequency and sampling frequency (e.g., number of samples per scan). These parameters can be selected to advantageously permit measuring absolute particle size and shape. Prior flow cytometers do not provide the ability to make such measurements.

In the image flow cytometer 100, the deflector 23 (FIG. 3A) scans the laser light, i.e., moves the irradiation location, in an X-direction and a substantially perpendicular Y-direction. In this example, the Y-direction is the direction of flow of fluid in the micro flow channel 12. The frequency for laser scanning can be, e.g., 1 MHz. In an example, when the flow rate of the microparticulate samples is 1 m/s, the laser light completes one cycle in the X-direction (across the microparticulate sample and back) while the microparticulate samples move by 1 μm in the Y-direction. In FIG. 8A, scanning path 63 shows the effect of scanning the irradiation location in the X-direction while moving the microparticulate sample 61 in the Y-direction. The irradiation location is rasterized over the microparticulate sample 61 to successively and individually irradiate many points or structures within the microparticulate sample 61. Various aspects advantageously provide particle flows with constant velocity on the Y-axis. Therefore, with only X-axis scanning, a two-dimensional image can be produced. This is unlike laser scanning confocal microscopes (e.g., the ZEISS LSM 710), in which a stationary sample is rasterized with a two-axis scanning device such as an X-Y galvanomirror. Two-axis scanners require significantly more moving parts and are more mechanically complex than one-axis scanners. Using a one-axis scanner advantageously permits simpler, more reliable construction. Additionally, using a flow permits measuring large numbers of microparticulate samples 61 in quick succession. Laser-scanning confocal microscopes requires samples to be prepared, e.g., on slides, and the focal point of the microscope to be moved to focus on the samples. Various aspects described herein do not require these steps, and produce two-dimensional data without them.

For example, when the microparticulate samples are neutrophils (diameter of 12 to 15μm), which are one kind of leucocytes, the neutrophils can be scanned at about 12 to 15 X-direction cycles per microparticulate sample 61 (for example, a scanning path 63 shown in FIG. 8A). In this case, in the about 12 to 15 cycles during which the neutrophils are scanned, the light intensity of the transmitted light detected by the photodetector 34 (FIG. 4A) and the light intensity of the forward-scattered light detected by the photodetector 35 (FIG. 4A) vary. For example, when the irradiation spot of the laser light is located on or within a neutrophil, the intensity of the transmitted light decreases and the intensity of the forward-scattered light increases due to reflection, scattering, absorption, or the like by the neutrophil. On the other hand, when the irradiation spot of the laser light deviates from (does not irradiate) any neutrophil, the laser light is not reflected, scattered, and absorbed by a neutrophil, so that the intensity of the transmitted light increases and the intensity of the forward-scattered light decreases compared to when the irradiation spot is located on or within a neutrophil.

In various aspects, control unit 5 processes signals from the detection optical systems 2 and 3 to determine properties of features within a microparticulate sample or other object. For example, individual mitochondria within a cell can be located using fluorescent tagging of mitochondria, e.g., with LIFE TECHNOLOGIES MITOSOX red mitochondrial superoxide indicator. As the irradiation spot is scanned over a cell that has been dyed with MITOSOX, red fluorescence will be detected when the irradiation spot is over a live mitochondrion. In this way, positions, counts, and distributions of mitochondria in a cell can be determined. In another example, dyes such as DHR 123 can be used similarly for detecting mitochondria.

Internal structures of other objects can also be determined. For example, any internal structure such as a labeled nucleus can be identified and distinguished from surrounding organelles. Other organelles can also be identified. In another example, in-situ hybridization problems can be clearly identified, as can mRNA. RNA transcripts can be identified by different fluorescent probes.

The control unit 5 can detect a variation of the light intensity of the transmitted light by the detection signal SIG_T (FIG. 4A), and can observe a variation of the light intensity of the fluorescence by the detection signals SIG_f1 to SIG_f3 (FIG. 5). FIG. 8B is a graph showing the scanning of the irradiation location in the X direction (first increasing, then decreasing) over time. FIG. 8C is a graph showing the intensity of the detection signal SIG_T which is detected by the control unit 5. In FIG. 8C, the horizontal axis represents time (t). Ranges 861 represent the time the irradiation spot is in or on microparticulate sample 61. As is seen from the graph, when the spot of the laser light is scanned in the X-axis direction and the spot of the laser light is located on each microparticulate sample 61 (in ranges 861), the level of the detection signal SIG_T decreases compared to its level when outside microparticulate sample 61 (ranges 861).

In various aspects, the flow rate of the microparticulate samples within the micro flow channel 12 is set by the control unit 5, e.g., by providing a control signal to a flow-inducing device such as a pump. In other aspects, the control unit 5 receives an indication of the flow rate from an external flow controller (not shown). Similarly, the control unit 5 can operate the irradiation optical system 2 to control the intensity of the incident light, or can receive information on the intensity of the light from an external light controller (not shown). In any of these aspects, the control unit 5 can obtain a two-dimensional distribution of the light intensity of each neutrophil from the information on the light intensity and the flow rate.

As described above, in this configuration, the laser light L is focused or otherwise directed to converge onto an area smaller than each microparticulate sample. (Alternatively, a laser with a core size smaller than the microparticulate sample can be used, and the beam directed to scan the microparticulate sample.) Accordingly, in this configuration, a profile of local scattered light and the like can be obtained by scanning the microparticulate samples. When the scanning rate, the scanning direction, and the flow rate of the microparticulate samples are taken into consideration based on this profile, a two-dimensional image of each microparticulate sample can be obtained. That is, according to this configuration, the form of each microparticulate sample can be directly observed by observing transmitted light, without using the fluorescence. Current cytometers measure averaged size and cell complexity using forward- and side-scattering signals. Even fluorescence does not provide information regarding shape of individual cells. In conventional cytometers, calibration beads of a known size are measured to determine the corresponding scattered-light intensities. Measured intensities from cells are then compared to the intensities from the calibration beads to infer size. This process requires a calibration step and does not provide a high level of accuracy of the results. In contrast, inventive scanning image cytometers described herein can provide 2-D transmission images with polarization (SIG_Tp and SIG_Ts, FIG. 4B) and fluorescence with (x, y) location (SIG_fn, n∈[1,2,3], FIG. 5). Combining two images can provide the full shape, structure, and fluorescence of a cell or other microparticulate sample with (x, y) location. In various aspects, using multiple two-dimensional images, a three-dimensional structure can be determined for the microparticulate sample. The determined 3-D structure can be processed to determine the locations of fluorescence probes in a microparticulate sample.

Hereinafter, other advantages obtained in this configuration will be described. In this configuration, the laser light radiated onto each sample is focused or directed to converge to a spot of size set by the diffraction limit of the optical system, which increases the light density. This improves the sample detection sensitivity and spatial resolution. In an example, the irradiation spot for a laser with wavelength k has a diameter between $\lambda/1.4$ and $\lambda/2$. As a result, a very small microparticulate sample, e.g., a submicrometer-sized to nanometer (nm)-sized sample, such as virus can be detected. Such small samples cannot be detected in prior flow cytometers. Furthermore, since the laser light is directed to irradiate a very small area, the total light output of the laser source can be reduced as compared with the typical flow cytometer, without reducing the irradiance (W/m$^2$). In various aspects, the irradiation optical system 2 is configured to provide an irradiance on the microparticulate sample selected based on the properties of the microparticulate sample, of any fluorescent dyes therein, or of other components or structures to be measured.

In various examples, the incident-light spot diameter d is characterized by the following equation:

$$d = k\lambda/NA$$

for numerical aperture NA and wavelength λ. In an example, k=0.82 for a spot diameter measured at $1/e^2$ or 0.48 for a spot diameter measured at FWHM. "$1/e^2$" refers to the perimeter around the spot where the intensity is $1/e^2 \approx 0.135$ of the peak intensity of the spot; "FWHM" refers to that perimeter at 50% of the peak intensity. Therefore, a 0.2 µm spot size can be used. Prior flow cytometers use, e.g., 10×70 µm spots. Various inventive examples herein therefore provide >10,000 times the area resolution of such comparative schemes.

In this configuration, as described above, the shape of each microparticulate sample can be obtained as a two-dimensional image. Accordingly, specific information such as the size (diameter) and shape (outline) of each microparticulate sample can be obtained from the two-dimensional image. Further, the classification of samples to be observed, for example, the type of cells to be used as biological samples, can be discriminated based on the size and shape of each microparticulate sample, without using a fluorescence spectral analysis. Some prior systems differentiate cell types using, e.g., fluorescent-dyed antibodies. The fluorescent light emitted under laser illumination indicates the type of antibody, and thus the type of cell to which the antibody is bound. However, this requires that a sufficient number of antibodies bind to the cell to produce a detectable amount of fluorescent light. In contrast, in this configuration, cell type can be determined directly. This advantageously reduces the probability of mis-identification of cell type owing to insufficient bonding of antibodies. It also permits discriminating between two cell types that have different shapes but that carry the same antigens and thus bond to the same antibodies.

In this and other exemplary configurations, a confocal optical system is used as the optical system for detecting transmitted light. The confocal optical system includes the laser source 21 and objective lens 24 (both FIG. 3A) that provide localized illumination, and pinhole 36 (FIG. 4A) that blocks out-of-focus light. This advantageously permits observation with a resolution substantially equivalent to the resolution of an observation of microparticulate samples with a laser confocal microscope. Consequently, image information on the surface and internal structure of each microparticulate sample can be obtained with high accuracy.

In a typical flow cytometer that applies a large beam spot to a sample, the light intensity of the beam spot has a distribution (for example, a Gaussian distribution). Accordingly, a variation occurs in the detection sensitivity depending on the position of the sample within the beam spot. For example, if the microparticulate sample is not centered in the irradiation area of a conventional flow cytometer, the signal intensity will be lower than if the microparticulate sample is centered in that irradiation area. On the other hand, in various inventive aspects described herein, including this configuration, the beam spot is smaller than the microparticulate sample. This significantly reduces, and can almost eliminate, variation of the detection sensitivity due to sample position.

This can also substantially reduce variation due to the light intensity distribution of the laser irradiation spot within the linear sweep range. A small spot scanned across a microparticulate sample can provide uniform illumination within an area of constant scan velocity. Some prior schemes are somewhat analogous to thick-nib permanent markers: coverage is heavier (light intensity is greater or ink is darker) in the center of the swept area than at the edges. Using a small spot can advantageously reduce the center-to-edge rolloff of light intensity.

In an exemplary configuration, a two-dimensional image is generated by utilizing the flow of microparticulate samples in the Y-direction for the scanning in the Y-direction. In addition, the scanning frequency in the X-direction can be set to be equal to or higher than 1 MHz, which alleviates prior limitations on the movement rate of the microparticulate samples and permits increasing the flow rate to the blood flow rate of a human body or higher.

A conventional flow cytometer requires labeling on microparticulate samples by using a fluorescent substance as a labeled substance (e.g., using antibodies, as discussed above). This causes problems in that it can take a great deal of time to perform preparatory work, and the survival rate and purity of biological samples can be adversely affected during an observation of biological cells, for example. However, the image flow cytometer according to this exemplary embodiment enables non-labeling cell measurement, i.e., measurement without labeling with a fluorescent substance. Therefore, the cell measurement can be achieved without the need for preparatory work and without any adverse effect on the survival rate and purity of biological samples.

In various aspects, image flow cytometer 100 for observing a microparticulate sample 61 includes the flow chamber 1. The flow chamber 1 includes a flow channel 12 formed therein to permit the microparticulate sample 61 to flow through the flow channel 12 in a flow direction, e.g., +Y. At least one irradiation optical system, e.g., irradiation optical system 2, is adapted to irradiate the microparticulate sample 61 in the flow channel 12 with incident light L in an irradiation spot smaller than a selected representative size. The representative size can be selected according to the properties of microparticulate samples 61 or other objects to be observed. For example, as discussed above, blood cells can have diameters ~10µm. The representative size can be set to >2µm FWHM, e.g., 3µm FWHM, and a 2µm spot (smaller than 3µm) can be used. Irradiation optical system 2 also scans an irradiation position of the irradiation spot substantially in a direction perpendicular to the flow direction (e.g., ±X, FIG. 8A). At least one detection optical system, e.g., system 3 or 4, detects a light intensity of resultant light (e.g., L_T-FS, L_T-SS, Lf) from the flow chamber 1. The detection optical system 3 is opposed to the irradiation optical system 2 through the flow chamber 1. Alternatively, a detection optical system (e.g., system 4) can be disposed at a position deviating from an optical axis of the incident light. An FS detector does not have to be exactly on the optical axis of the incident light L (FIG. 1), but can be, e.g., within ±1°, ±5°, ±10°, or ±15° of the optical axis. A control unit 5 detects the microparticulate sample according to a change of the light intensity of the resultant light detected by the detection optical system 3.

Second Exemplary Embodiment

Figure 9:
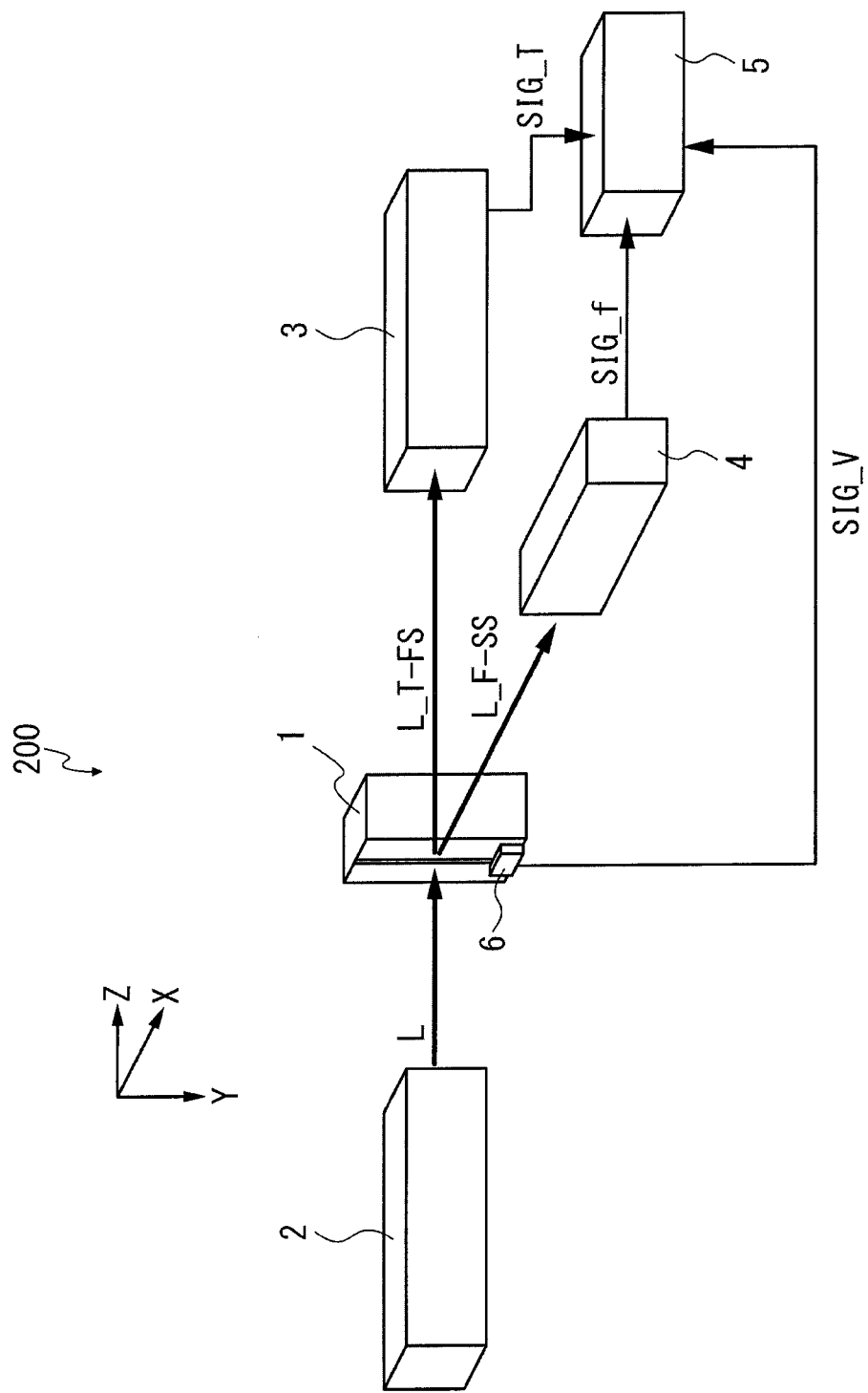
FIG. 9 is a configuration diagram showing a schematic configuration of an image flow cytometer 200 according to a second exemplary embodiment.

Next, an image flow cytometer 200 according to a second exemplary embodiment will be described. The image flow cytometer 200 can be a scanning-type image flow cytometer. FIG. 9 is a configuration diagram showing a schematic configuration of the image flow cytometer 200 according to the second exemplary embodiment. The image flow cytometer 200 has a configuration in which a flow rate measuring device 6 is added to the image flow cytometer 100 according to an exemplary embodiment.

The flow rate measuring device 6 is disposed in the micro flow channel 12 of the flow chamber 1 or in another flow channel connected to the micro flow channel 12, and measures the flow rate of microparticulate samples or liquid within the micro flow channel 12. In this case, a flow rate in the vicinity of the center of the micro flow channel 12 (that is, a peak value of the flow rate within the micro flow channel 12 in a certain section), for example, is desirably measured. The flow rate measuring device 6 outputs a flow rate signal SIG_V, which represents the measured flow rate, to the control unit 5.

The control unit 5 reads, from the flow rate signal SIG_V, a flow rate Vf of the microparticulate samples or liquid within the micro flow channel 12. Further, the control unit 5 performs arithmetic processing using the read flow rate Vf, thereby generating a two-dimensional image of each microparticulate sample. In an example, the control unit 5 uses the read flow rate Vf to determine the amount of Y distance the microparticulate sample 61 (FIG. 8A) travels in each cycle of the irradiation location in the X-direction.

The control unit 5 generates a two-dimensional image of each microparticulate sample by using a predetermined flow rate. In practice, the flow rate within the micro flow channel 12 can vary due to, e.g., external factors such as temperature (which can affect fluid viscosity). If the variation in the flow rate increases, and the increased variation is not taken into account, there is a possibility that the two-dimensional image obtained by the operation can be distorted and deviate from the actual shape of each microparticulate sample.

In this configuration, therefore, the flow rate measuring device 6 monitors the flow rate Vf within the micro flow channel 12 in real time. The control unit 5 generates a two-dimensional image of each microparticulate sample while updating the flow rate for use in generating the two-dimensional image with the latest flow rate Vf. Accordingly, this and similar aspects permit producing a two-dimensional image with reduced distortion, even when the flow rate Vf varies. Therefore, according to this configuration, it is possible to obtain a two-dimensional image of each microparticulate sample with high accuracy.

Third Exemplary Embodiment

Figure 10:
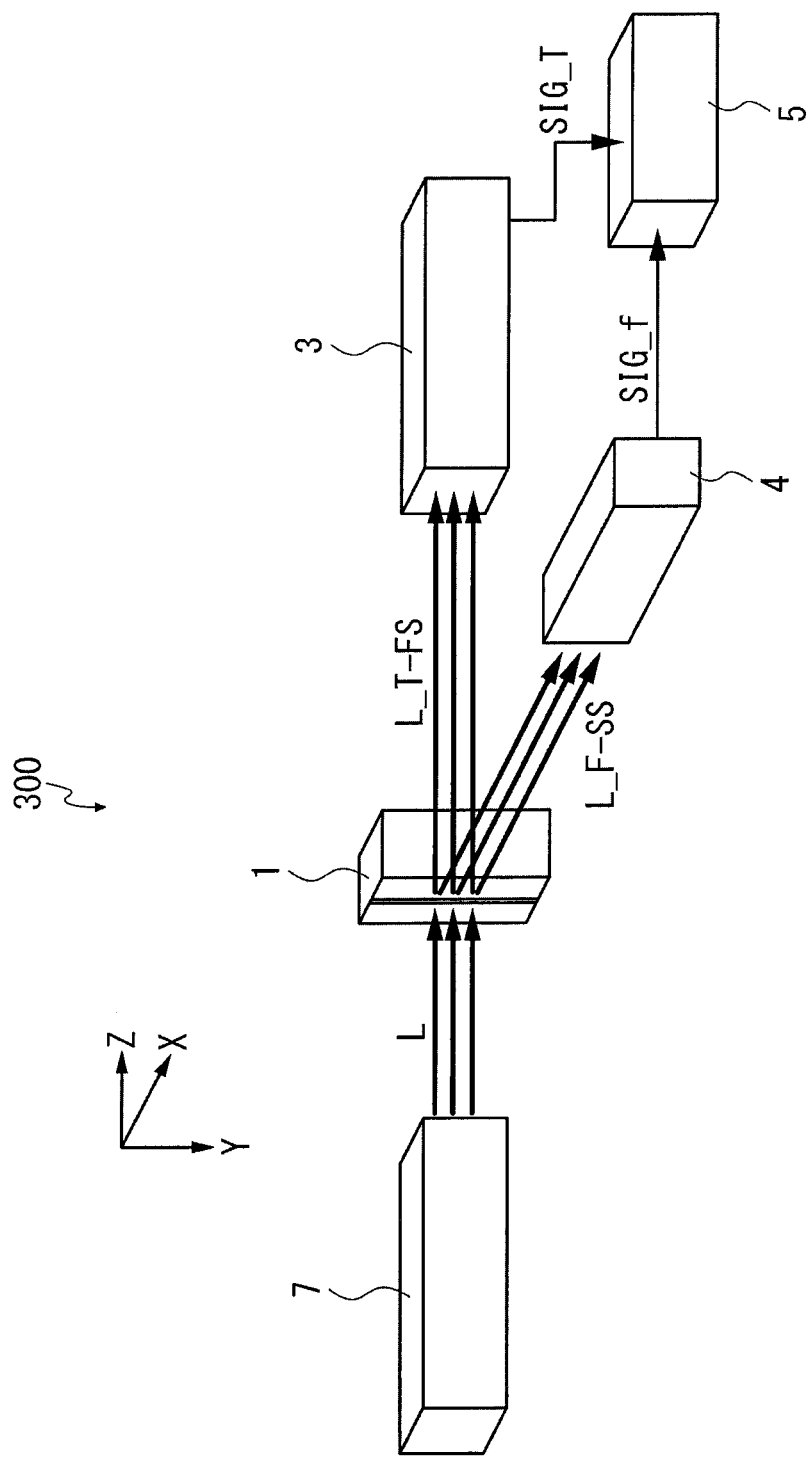
FIG. 10 is a configuration diagram showing a schematic configuration of an image flow cytometer 300 according to a third exemplary embodiment.

Next, an image flow cytometer 300 according to a third exemplary embodiment will be described. The image flow cytometer 300 can be a scanning-type image flow cytometer. FIG. 10 is a configuration diagram showing a schematic configuration of the image flow cytometer 300 according to the third exemplary embodiment. The image flow cytometer 300 has a configuration in which the irradiation optical system 2 of the image flow cytometer 100 according to the first exemplary embodiment is replaced by an irradiation optical system 7.

Figure 11:
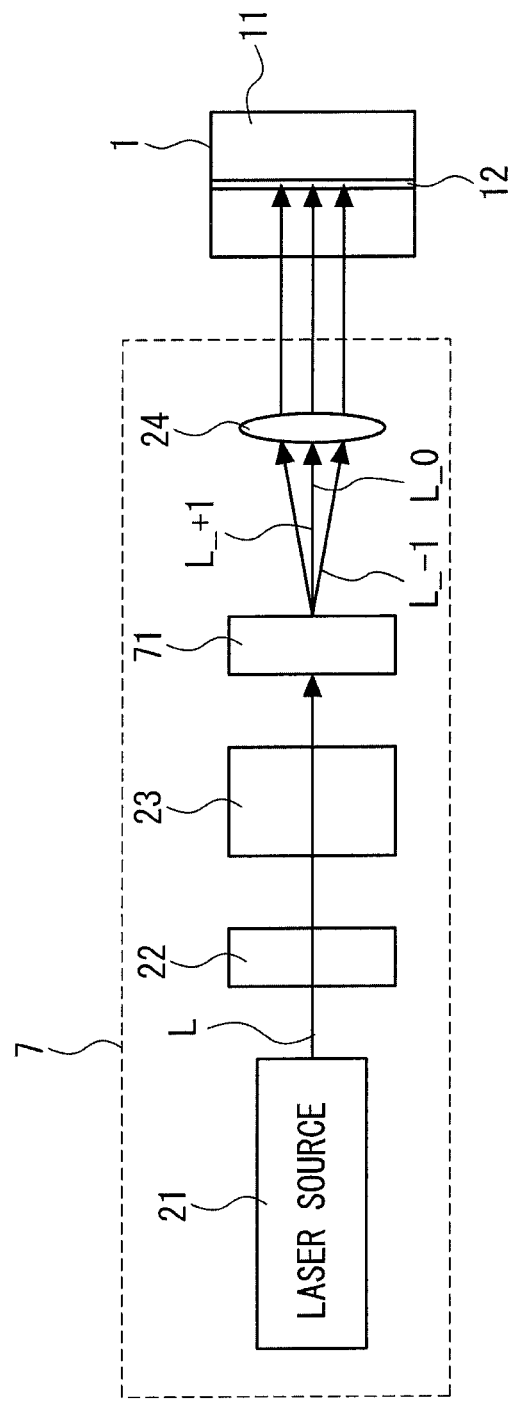
FIG. 11 is a block diagram schematically showing a configuration of an exemplary irradiation optical system 7.

FIG. 11 is a block diagram schematically showing the configuration of an exemplary irradiation optical system 7. The irradiation optical system 7 has a configuration in which a diffraction grating, e.g., phase diffraction grating 71, is added to the irradiation optical system 2. The phase diffraction grating 71 is disposed between the deflector 23 and the objective lens 24. The laser light L is diffracted by the phase diffraction grating 71, so that zero-order diffracted light $L\_0$, plus-first-order diffracted light $L\_{+1}$, and minus-first-order diffracted light $L\_{-1}$ are generated. The objective lens 24 is designed to cause the zero-order diffracted light $L\_0$, the plus-first-order diffracted light $L\_{+1}$, and the minus-first-order diffracted light $L\_{-1}$ to converge to the diffraction limit at different positions in the Y-direction (shown in FIG. 10) of the micro flow channel 12 of the flow chamber 1.

In various configurations, when the laser light L is diffracted by the phase diffraction grating 71, the diffracted light having an order greater than ±1 is generated. However, the diffracted light having a large order has a large diffraction angle, which may cause a situation in which the diffracted light is not incident on the objective lens 24, or the focal point position is liable to deviate from the micro flow channel 12 even when the diffracted light is incident on the objective lens 24. Further, the diffracted light having a large order has a small light intensity. An exemplary phase grating can provide over 90% of the incident intensity within the first-order, so higher-order spots can have negligible intensity. Accordingly, various examples herein assume that the diffracted light having an order greater than ±1 is not used for detection. However, this does not preclude the use of the diffracted light having an order greater than ±1 for detection. Such light can be used by suitably configuring the objective lens 24, or by adding other components such as mirrors to direct the ±2 order and above. In various aspects, only positive order(s), or only negative order(s), of diffracted light are used with the zero-order light (e.g., 0 and +1 or 0 and −1).

The zero-order diffracted light $L\_0$, the plus-first-order diffracted light $L\_{+1}$, and the minus-first-order diffracted light $L\_{-1}$ are focused at different positions spaced apart from each other in the Y-direction in the micro flow channel 12. As in the first exemplary embodiment, transmitted light, forward-scattered light, fluorescence, and side-scattered light are generated from each of the zero-order diffracted light $L\_0$, the plus-first-order diffracted light $L\_{+1}$, and the minus-first-order diffracted light $L\_{-1}$ which are focused in the micro flow channel 12.

Figure 12:
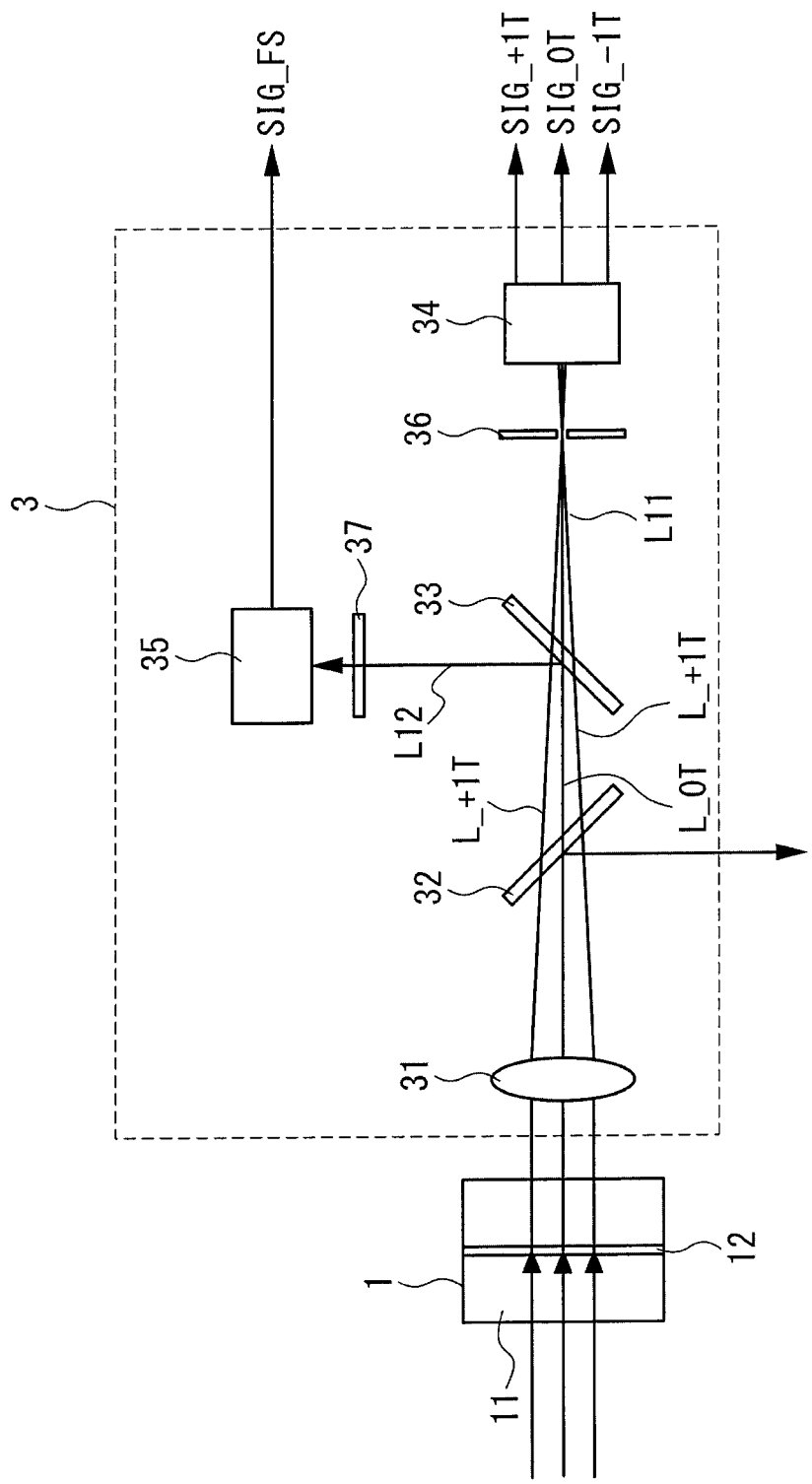
FIG. 12 is a configuration diagram schematically showing an exemplary configuration of the detection optical system 3 of the image flow cytometer 300.

Referring to FIG. 12, the transmitted light of the zero-order diffracted light $L\_0$ is transmitted light $L\_0T$. The transmitted light of the plus-first-order diffracted light $L\_{+1}$ is transmitted light $L\_{+1}T$. The transmitted light of the minus-first-order diffracted light $L\_{-1}$ is transmitted light $L\_{-1}T$. FIG. 12 is a configuration diagram schematically showing an exemplary configuration of the detection optical system 3 of the image flow cytometer 300. The objective lens 31 of the detection optical system 3 is arranged to cause the transmitted light $L\_0T$ of the zero-order diffracted light, the transmitted light $L\_{+1}T$ of the first-order diffracted light, and the transmitted light $L\_{-1}T$ of the minus-first-order diffracted light to form an image at different positions on the receiving surface of the photodetector 34. Accordingly, the photodetector 34 can receive, in a distinguishable manner, the transmitted light $L\_0T$ of the zero-order diffracted light, the transmitted light $L\_{+1}T$ of the first-order diffracted light, and the transmitted light $L\_{-1}T$ of the minus-first-order diffracted light. The photodetector 34 outputs, to the control unit 5, signal SIG_0T representing the transmitted light $L\_0T$ of the zero-order diffracted light, signal SIG_+1T representing the transmitted light $L\_{+1}T$ of the first-order diffracted light, and signal SIG_−1T representing the transmitted light $L\_{-1}T$ of the minus-first-order diffracted light.

Figure 13:
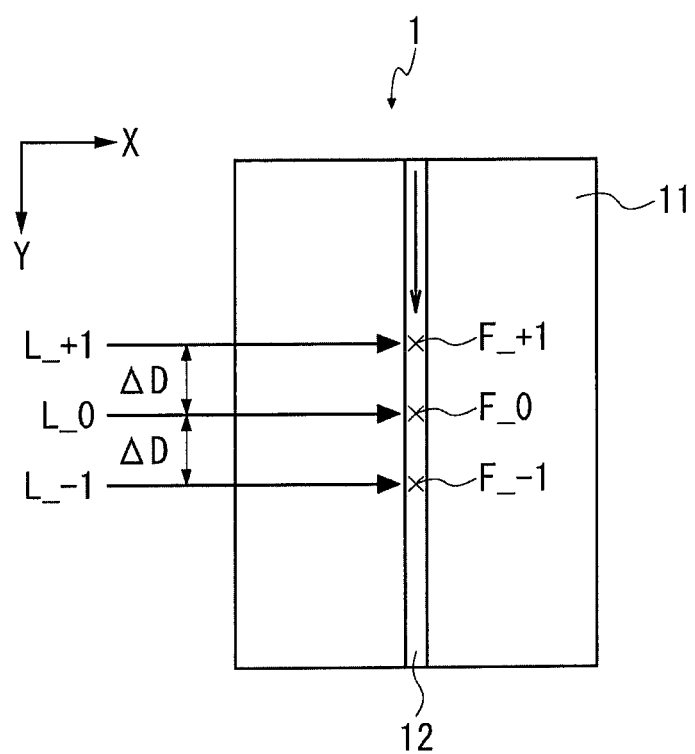
FIG. 13 is an enlarged view showing the vicinity of the micro flow channel 12 of the image flow cytometer 300 according to various aspects.

The operation of the exemplary image flow cytometer 300 will be described. FIG. 13 is an enlarged front view showing the vicinity of the micro flow channel 12 of the image flow cytometer 300. In the micro flow channel 12 of the image flow cytometer 300, the microparticulate samples 61 sequentially pass through a focal position $F\_{+1}$ of the plus-first-order diffracted light $L\_{+1}$, a focal position $F\_0$ of the zero-order diffracted light $L\_0$, and a focal position $F\_{-1}$ of the minus-first-order diffracted light $L\_{-1}$, in the stated order. The focal positions are marked with "X" signs to indicate that, in this view, laser light L (FIG. 10) is passing from in front of the plane of the figure to behind the plane of the figure.

This enables the control unit 5 to observe a sequential change of a signal SIG_+1T, a detection signal SIG_0T, and a signal SIG_−1T. The distances between the focal point position $F\_{+1}$ of the plus-first-order diffracted light $L\_{+1}$, the focal point position $F\_0$ of the zero-order diffracted light $L\_0$, and the focal position $F\_{-1}$ of the minus-first-order diffracted light $L\_{-1}$ are known values uniquely determined from the layout of the phase diffraction grating 71, the objective lens 24, and the micro flow channel 12; the grating pitch of the phase diffraction grating 71; and the NA (numerical aperture) of the objective lens 24. In an example, the distance between the focal position $F\_{+1}$ of the plus-first-order diffracted light $L\_{+1}$ and the focal position $F\_0$ of the zero-order diffracted light L_0 is ΔD. Similarly, the distance between the focal position F_0 of the zero-order diffracted light L_0 and the focal position F_−1 of the minus-first-order diffracted light L_−1 is ΔD. In an example, ΔD is 25-5 μm.

In an example, laser light L is diffraction-limited and the objective lens 24 has a numerical aperture (NA) of 0.15 and a focal length of 20 mm. The spot separation ΔD=20 um at 1 m/s sample flow. All samples can be detected for up to 25,000 cells/sec. The time between spots is ~20 us or ~40 us.

In various aspects, higher resolution is achieved by stitching, e.g., three images. This can improve the scan resolution from 1 μm to 0.3 μm.

In another example, NA=0.75. The +/−1st order light beams have an angle of 30° with the object to be tested. This permits determining a 3-D image or structure of the object. In this and other examples, the 3-D image can be represented as a voxel array, as polygons, or in other representations. Objects to be tested can be of various sizes.

Figure 14:
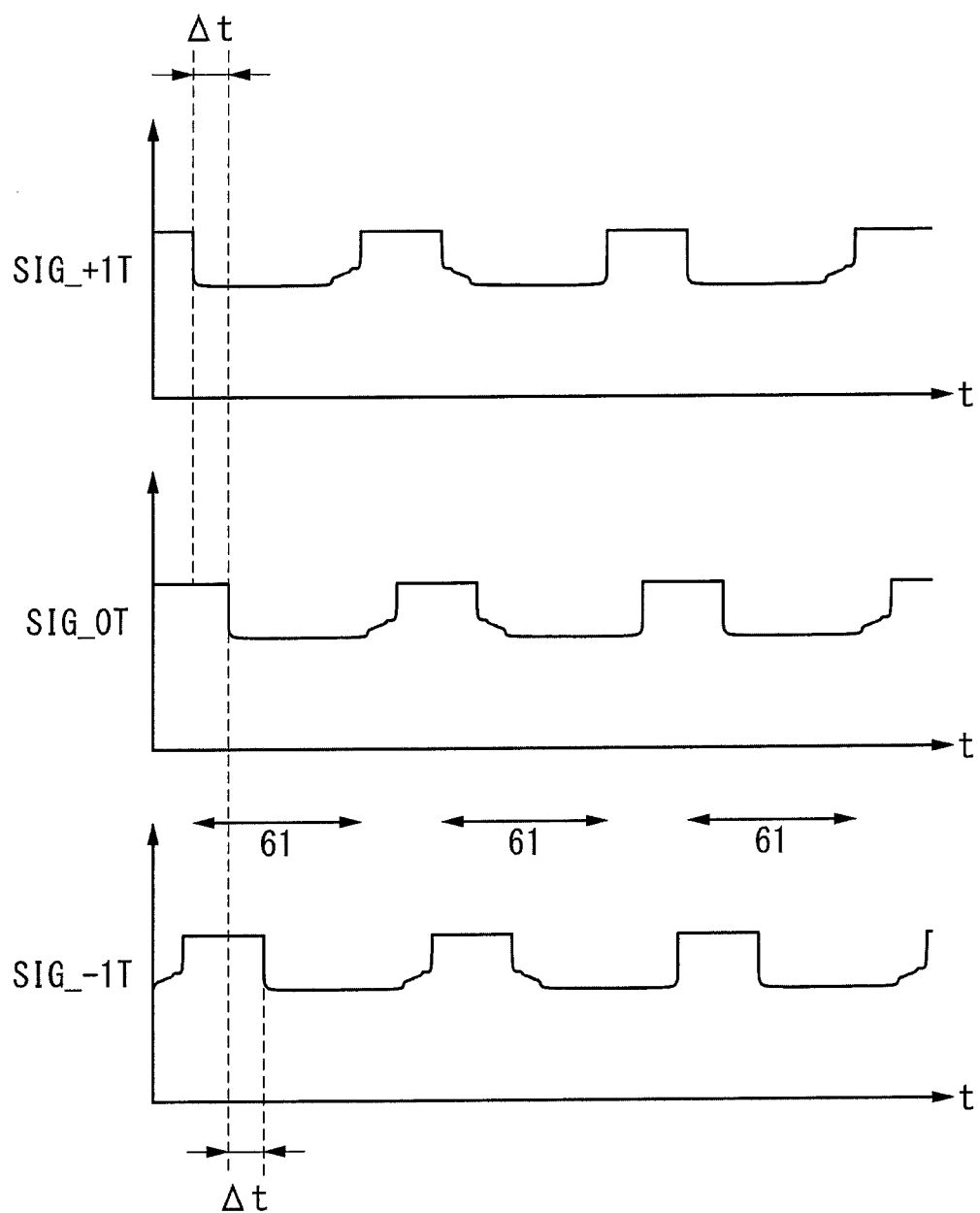
FIG. 14 is a timing diagram showing a variation of each of a detection signal SIG_+1T, a detection signal SIG_0T, and a detection signal SIG_−1T, according to an example.

FIG. 14 is a timing diagram showing variations of the detection signal SIG_+1T, the detection signal SIG_0T, and the detection signal SIG_−1T, in this example. In this case, the control unit 5 can observe a time interval Δt between changes of the detection signal SIG_+1T, the detection signal SIG_0T, and the detection signal SIG_−1T. Accordingly, the control unit 5 can calculate the flow rate Vf of the microparticulate samples within the micro flow channel 12 based on the distance ΔD and the time interval Δt: Vf=ΔD/Δt. Thus, the control unit 5 performs arithmetic processing using the flow rate Vf in the same manner as in the second exemplary embodiment, thereby making it possible to generate a two-dimensional image of each microparticulate sample.

In this configuration, the control unit 5 can monitor the flow rate Vf within the micro flow channel 12 in real time. This enables the control unit 5 to generate a two-dimensional image of each microparticulate sample while reflecting the variation of the flow rate Vf. Thus, according to this configuration, as compared with the first exemplary embodiment, a distortion of a two-dimensional image to be generated can be reduced even when the flow rate Vf varies. Therefore, according to this configuration, it is possible to obtain a two-dimensional image of each microparticulate sample with high accuracy.

Note that the second exemplary embodiment illustrates an example in which the flow rate measurement device 6 is provided as an example of flow rate measurement means. On the other hand, in this configuration, the phase diffraction grating 71 and the control unit 5 collaborate with each other to obtain the flow rate Vf of the microparticulate samples within the micro flow channel 12. Accordingly, in this exemplary embodiment, it can also be understood that the phase diffraction grating 71 and the control unit 5 constitute a flow rate measurement device. A flow rate measurement device 6 can also be used in combination with the phase diffraction grating 71 and the control unit 5, e.g., to reduce noise in determinations of Vf.

Figure 15:
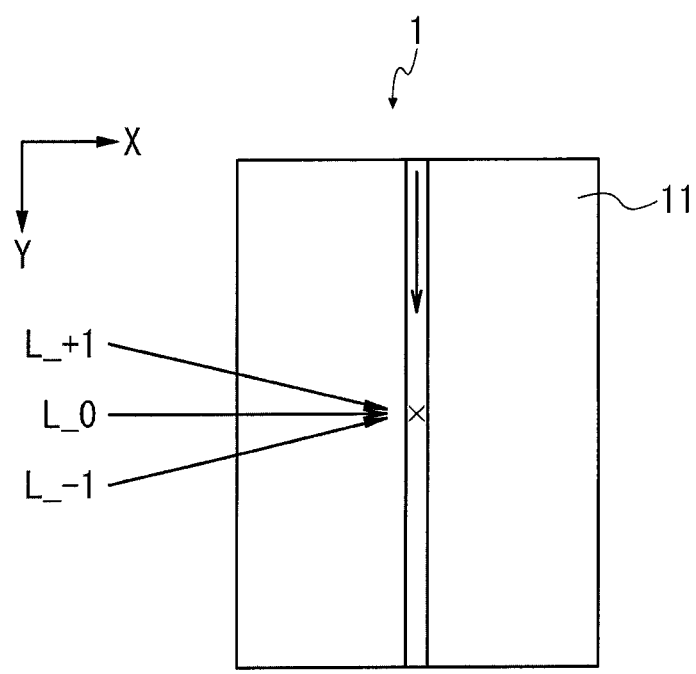
FIG. 15 is an enlarged view showing the vicinity of the micro flow channel 12 in an example in which a plus-first-order diffracted light L_+1, a zero-order diffracted light L_0, and a minus-first-order diffracted light L_−1 are made incident on the same position.

This exemplary embodiment illustrates the case where the plus-first-order diffracted light L_+1, the zero-order diffracted light L_0, and the minus-first-order diffracted light L_−1 are incident on the micro flow channel 12 in parallel. However, the plus-first-order diffracted light L_+1, the zero-order diffracted light L_0, and the minus-first-order diffracted light L_−1 can also be made incident on the same position by designing objective lens 24 to cause those orders of light to converge. FIG. 15 is an enlarged view of the micro flow channel 12 when the plus-first-order diffracted light L_+1, the zero-order diffracted light L_0, and the minus-first-order diffracted light L_−1 are made incident on the same position "X". In this case, the flow rate Vf is not calculated as described above with reference to FIG. 14. Vf can be determined, e.g., using a flow rate measurement device 6 (FIG. 9). In this example, the microparticulate samples can be irradiated with light from three different directions at the same time. Accordingly, the transmitted light, the scattered light, the fluorescence, and the like include information obtained from the light incident from three different directions. The control unit 5 can also analyze a three-dimensional structure of each microparticulate sample by appropriately processing the information obtained from the light incident from three different directions by means of a three-dimensional parallax. Light can also be directed from multiple directions onto a common position "X", e.g., from multiple lasers or light sources, or multiple optical fibers carrying light from a common light source to different positions with respect to the common position.

Figure 16A:
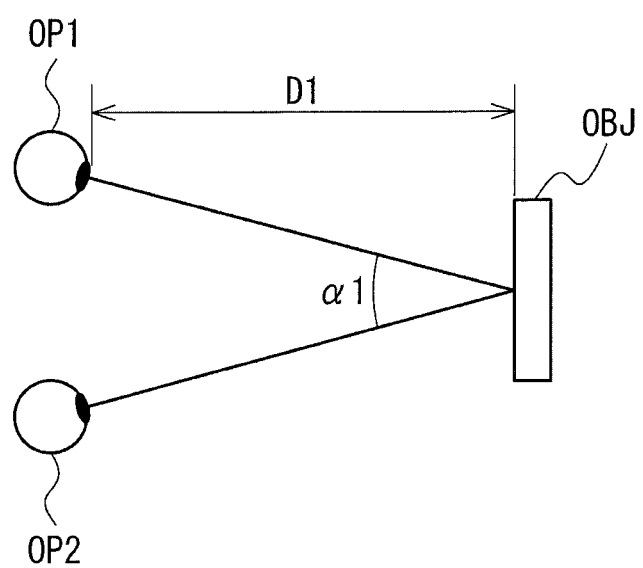
FIG. 16A is a view showing an example of parallax when a distance is long between an observation points and an observation object.
Figure 16B:
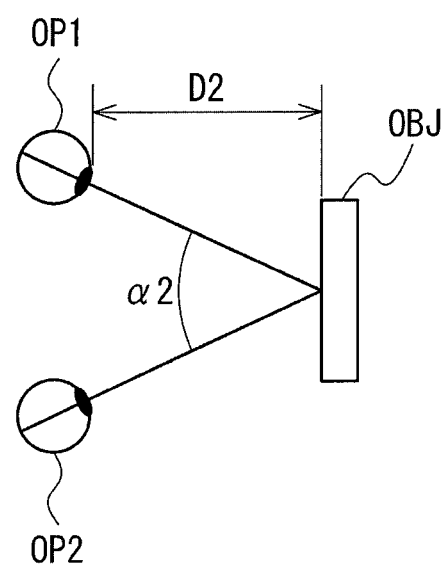
FIG. 16B is a view showing an example of parallax when a distance is short between the observation points and the observation object.

The three-dimensional parallax will be briefly described. FIG. 16A is a view showing a parallax when a distance is long between an observation points and an observed object. Shown in FIG. 16A, when a distance between the observation points OP1 and OP2, and the observed object OBJ, is D1, a parallax angle is α1. FIG. 16B is a view showing a parallax when a distance is short between the observation points and the observed object. Shown in FIG. 16B, when the horizontal distance between the observation points OP1 and OP2, and the observed object OBJ is D2, a parallax angle is α2. When D1 is greater than D2 (D1>D2), a1 is less than α2 (α1<α2).

Figure 16C:
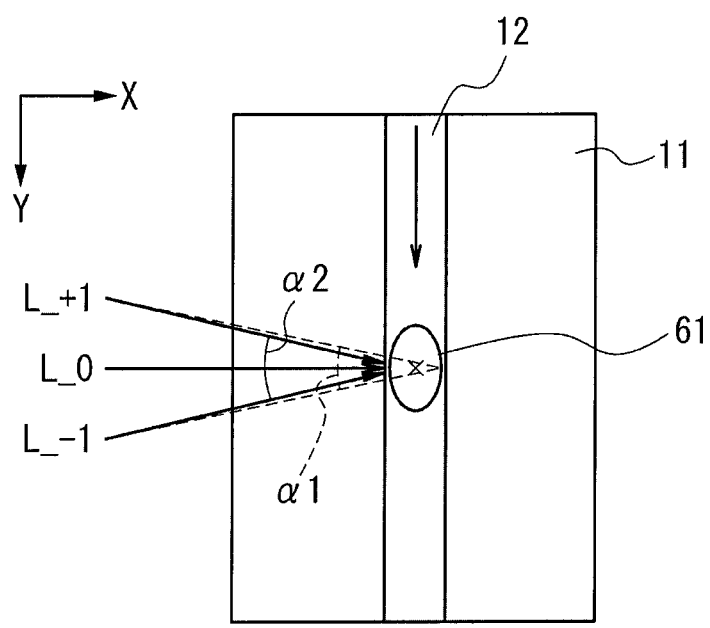
FIG. 16C is an enlarged view of a vicinity of the micro flow channel 12 showing the three-dimensional parallax according to various aspects.

FIG. 16C is an enlarged view of a vicinity of the micro flow channel 12 showing the three-dimensional parallax. In FIG. 16C, the microparticulate sample 61 corresponds to the observed object OBJ of FIGS. 16A, 16B. In FIG. 16C, D1 is a distance between the observation points OP1 and OP2 and the backside of the microparticulate sample 61. D2 is a distance between the observation points OP1 and OP2 and the front side of microparticulate sample 61. In this case, the three-dimensional parallax Δα can be expressed by following expression (2):

$$\Delta\alpha = \alpha2 - \alpha1 \qquad (2)$$

Therefore, three-dimensional data such as the steric configuration of the microparticulate sample 61 can be obtained by measuring Δα. There is many ways to create 3D images. In this example, two images with different Δα values are obtained by independently detecting signals of L_+1 and L_−1. This is similar to the way to consumer 3D televisions provide a 3D image. In various aspects, two 2-D scans can be combined to provide a 3-D dataset. Scans can be taken in the X-Y and X-Z planes.

Parallax affects the view of moving microparticulate samples 61 or other objects. For a certain distance the object moves, features of the object closer to the viewer move through a wider angular range than features farther from the viewer. This is indicated by FIGS. 16A and 16B, which show that the distance between the viewer's eyes subtends a larger angle α2 if the object is close than the angle α1 if the object is farther away. Referring back to FIG. 16C, features of the microparticulate sample 61 (e.g., mitochondria in a cell) are in different positions in the L_+1 image than in the L_−1 image. The closer the feature is to the irradiation optical system 7, the more different the positions will be in the two images. Therefore, the control unit 5 can locate common features in the L_+1, L_0, and L_−1 images (or any combination of those or any number of images at different angles). The controller can compare the positions of the corresponding features in the three images and use geometric and trigonometric relationships to infer the 3-D positions of those features within the microparticulate object 61. Features can include organelles, inclusions, defined portions of a cell membrane, or other objects smaller than, or contained within, the microparticulate sample 61.

Fourth Exemplary Embodiment

Figure 17:
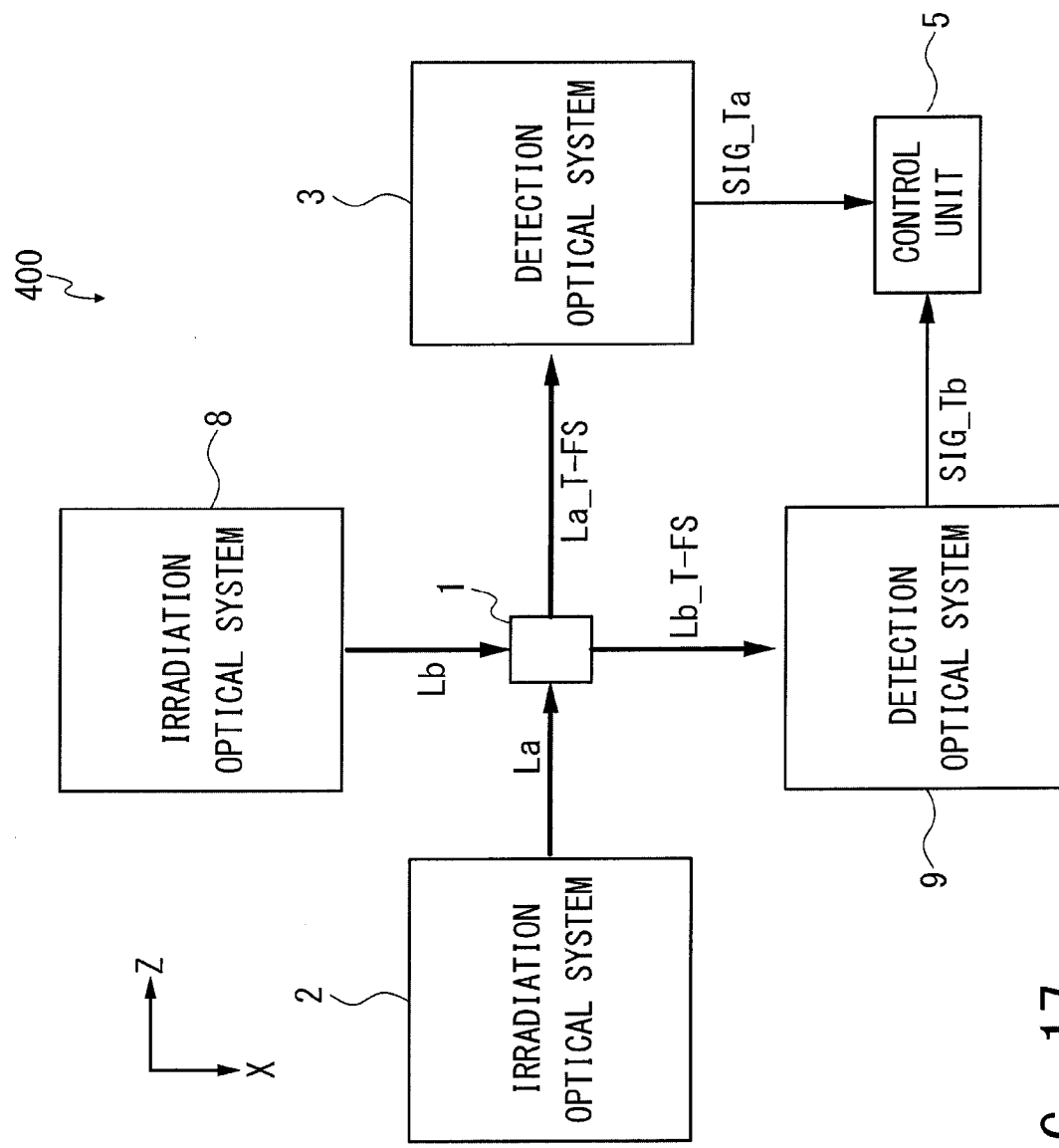
FIG. 17 is a configuration diagram showing a schematic configuration of an image flow cytometer 400 according to a fourth exemplary embodiment.

Next, an image flow cytometer 400 according to a fourth exemplary embodiment will be described. The image flow cytometer 400 can be a scanning-type image flow cytometer. FIG. 17 is a configuration diagram showing a schematic configuration of the image flow cytometer 400 according to the fourth exemplary embodiment. The image flow cytometer 400 has a configuration in which an additional irradiation optical system 8 and a detection optical system 9 are added to the image flow cytometer 100 according to an exemplary embodiment. To simplify the drawings, the illustration of the detection optical system 4 (FIG. 1) is omitted in FIG. 17. The detection optical system 4 can be used with systems 2, 3, 8, 9, or not. Four detection optical systems can also be used to provide forward- and side-scatter measurements along two different axes of incident light (e.g., light La, Lb).

The irradiation optical system 8 has a configuration similar to that of the irradiation optical system 2, and is disposed at a position rotated, e.g., by 90°, with respect to the irradiation optical system 2 around the flow chamber 1. The detection optical system 9 (referred to, without limitation on angle of placement or orientation, as a perpendicular detection optical system) has a configuration similar to that of the detection optical system 3 (the parallel detection optical system), and is disposed at a position opposed to the irradiation optical system 8 through the flow chamber 1. In this example, the irradiation optical system 8 and the detection optical system 9 are disposed in the X-Z plane. The irradiation optical system 8 and the detection optical system 9 can also be disposed in the X-Y plane or in other planes, e.g., at 45° to the X-Y, X-Z, or Y-Z planes. Referring back to FIG. 1, in an example, the irradiation optical systems 2, 8 and the detection optical systems 3, 9 are disposed in the X-Z plane, and the detection optical system 4 (for detecting side-scattered light L_F-SS corresponding to the irradiation optical system 2) is disposed in a plane that is the X-Z plane rotated a small amount around the Z-axis, e.g., 5°-85°, particularly 15°, 30°, 45°, or 60°.

In FIG. 17, incident light output from the irradiation optical system 2 is denoted "La," and incident light output from the irradiation optical system 8 is denoted "Lb." Transmitted light/forward-scattered light incident on the detection optical system 3 is labeled as transmitted light/forward-scattered light La_T-FS, and transmitted light/forward-scattered light incident on the detection optical system 9 is labeled as transmitted light/forward-scattered light Lb_T-FS. A detection signal output from the detection optical system 3 is a detection signal SIG_Ta, and a detection signal output from the detection optical system 9 is a detection signal SIG_Tb. The directions of light La, Lb can be substantially perpendicular, or not. Any number of irradiation-system/detection-system pairs can be used, at any angle in any plane, as long as the incident light from each is directed onto an appropriate portion of the flow chamber 1.

In an example, the detection optical system 3 detects first transmitted light as a part of the resultant light corresponding to incident light from the irradiation optical system 2. Further, the detection optical system 9 detects second transmitted light as a part of the resultant light corresponding to incident light from the irradiation optical system 8. The control unit 5 generates a three-dimensional image representing a steric structure of each microparticulate sample based on the two-dimensional image obtained from the detection signal SIG_Ta output from the detection optical system 3 and the two-dimensional image obtained from the detection signal SIG_Tb output from the detection optical system 9. For example, corresponding features can be identified in the two images. One image will provide the X coordinate of the identified feature, one image will provide the Z coordinate of the identified feature, and the measurement of time or flow distance will provide the Y coordinate of the identified feature.

According to this configuration, two pairs of optical systems including the irradiation optical systems and the transmitted light detection optical systems are provided at different angles, thereby facilitating observation of a three-dimensional structure of each microparticulate sample to be observed.

Exemplary Data-Processing Systems

Throughout this description, some aspects are described in terms that would ordinarily be implemented as software programs. Those skilled in the art will readily recognize that the equivalent of such software can also be constructed in hardware (hard-wired or programmable), firmware, or microcode. Accordingly, aspects of the present invention may take the form of an entirely hardware embodiment, an entirely software embodiment (including firmware, resident software, or micro-code), or an embodiment combining software and hardware aspects. Software, hardware, and combinations can all generally be referred to herein as a "service," "circuit," "circuitry," "module," or "system." Various aspects can be embodied as systems, methods, or computer program products. Because data manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Figure 18:
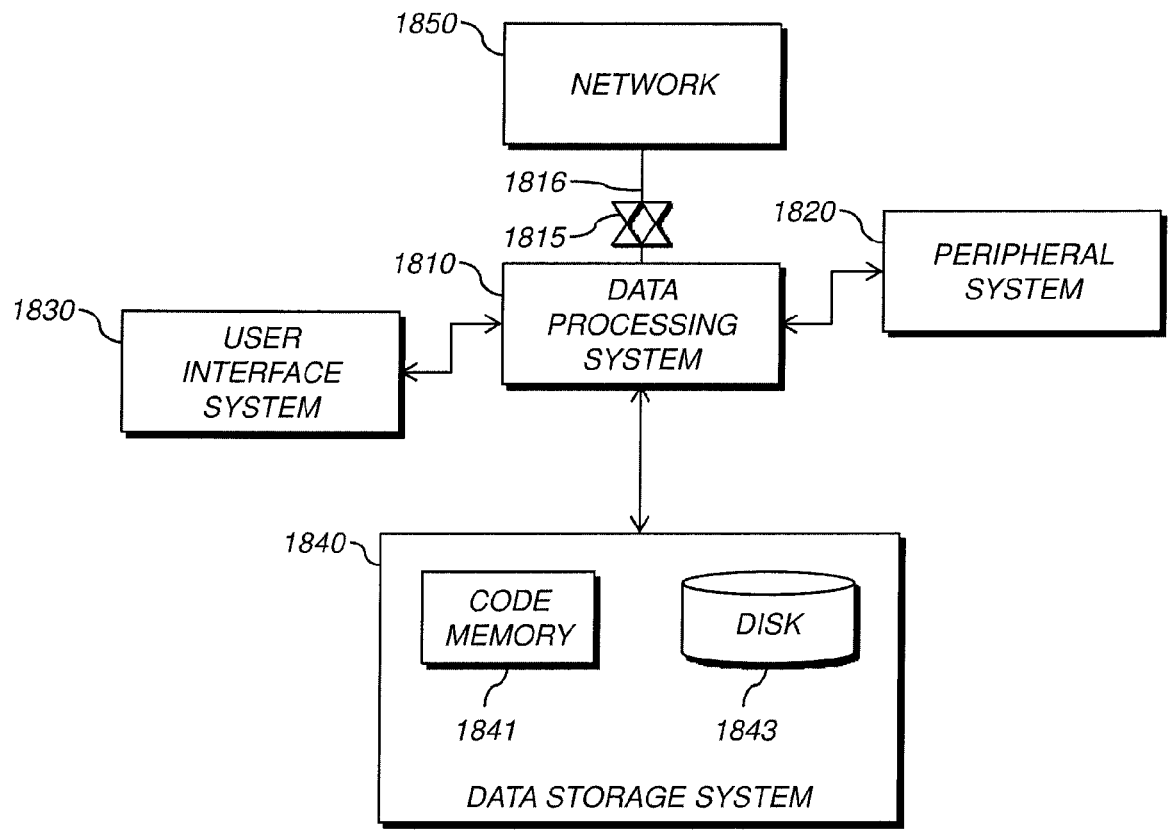
FIG. 18 is a high-level diagram showing components of a data-processing system.

FIG. 18 is a high-level diagram showing the components of an exemplary data-processing system for analyzing data and performing other analyses described herein. The system includes a data processing system 1810, a peripheral system 1820, a user interface system 1830, and a data storage system 1840. The peripheral system 1820, the user interface system 1830 and the data storage system 1840 are communicatively connected to the data processing system 1810. Data processing system 1810 can be communicatively connected to network 1850, e.g., the Internet or an X.25 network, as discussed below. Control unit 5 (FIG. 1, 6, 7, 9, 10, or 17) can include one or more of systems 1810, 1820, 1830, 1840, and can connect to one or more network(s) 1850. Data processing system 1810, and other processing devices described herein, can each include one or more microprocessors, microcontrollers, field-programmable gate arrays (FPGAs), programmable logic devices (PLDs), programmable logic arrays (PLAs), programmable array logic devices (PALs), or digital signal processors (DSPs).

The data processing system 1810 includes one or more data processor(s) that implement processes of various aspects described herein. A "data processor" is a device for automatically operating on data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise.

The phrase "communicatively connected" includes any type of connection, wired or wireless, between devices, data processors, or programs in which data can be communicated. Subsystems such as peripheral system 1820, user interface system 1830, and data storage system 1840 are shown separately from the data processing system 1810 but can be stored completely or partially within the data processing system 1810.

The data storage system 1840 includes or is communicatively connected with one or more tangible non-transitory computer-readable storage medium(s) configured to store information, including the information needed to execute processes according to various aspects. A "tangible non-transitory computer-readable storage medium" as used herein refers to any non-transitory device or article of manufacture that participates in storing instructions which may be provided to a data processing system 1810, e.g., in control unit 5, for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Aspects of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct data processing system 1810 to perform a particular series of operational steps when loaded, thereby implementing functions or acts specified herein.

In an example, data storage system 1840 includes code memory 1841, e.g., a random-access memory, and disk 1843, e.g., a tangible computer-readable rotational storage device such as a hard drive. Computer program instructions are read into code memory 1841 from disk 1843, or a wireless, wired, optical fiber, or other connection. Data processing system 1810 then executes one or more sequences of the computer program instructions loaded into code memory 1841, as a result performing process steps described herein. In this way, data processing system 1810 carries out a computer implemented process. For example, blocks of the flowchart illustrations or block diagrams herein, and combinations of those, can be implemented by computer program instructions. Code memory 1841 can also store data, or not: data processing system 1810 can include Harvard-architecture components, modified-Harvard-architecture components, or Von-Neumann-architecture components.

Computer program code can be written in any combination of one or more programming languages, e.g., JAVA, Smalltalk, C++, C, or an appropriate assembly language. Program code to carry out methods described herein can execute entirely on a single data processing system 1810 or on multiple communicatively-connected data processing systems 1810. For example, code can execute wholly or partly on a user's computer and wholly or partly on a remote computer or server. The server can be connected to the user's computer through network 1850.

The peripheral system 1820 can include one or more devices configured to provide digital content records to the data processing system 1810. For example, the peripheral system 1820 can include digital still cameras, digital video cameras, cellular phones, or other data processors. The data processing system 1810, upon receipt of digital content records from a device in the peripheral system 1820, can store such digital content records in the data storage system 1840.

The user interface system 1830 can include a mouse, a keyboard, another computer (connected, e.g., via a network or a null-modem cable), or any device or combination of devices from which data is input to the data processing system 1810. In this regard, although the peripheral system 1820 is shown separately from the user interface system 1830, the peripheral system 1820 can be included as part of the user interface system 1830.

The user interface system 1830 also can include a display device, a processor-accessible memory, or any device or combination of devices to which data is output by the data processing system 1810. In this regard, if the user interface system 1830 includes a processor-accessible memory, such memory can be part of the data storage system 1840 even though the user interface system 1830 and the data storage system 1840 are shown separately in FIG. 18.

In various aspects, data processing system 1810 includes communication interface 1815 that is coupled via network link 1816 to network 1850. For example, communication interface 1815 can be an integrated services digital network (ISDN) card or a modem to provide a data communication connection to a corresponding type of telephone line. As another example, communication interface 1815 can be a network card to provide a data communication connection to a compatible local-area network (LAN), e.g., an Ethernet LAN, or wide-area network (WAN). Wireless links, e.g., WiFi or GSM, can also be used. Communication interface 1815 sends and receives electrical, electromagnetic or optical signals that carry digital data streams representing various types of information across network link 1816 to network 1850. Network link 1816 can be connected to network 1850 via a switch, gateway, hub, router, or other networking device.

Network link 1816 can provide data communication through one or more networks to other data devices. For example, network link 1816 can provide a connection through a local network to a host computer or to data equipment operated by an Internet Service Provider (ISP).

Data processing system 1810 can send messages and receive data, including program code, through network 1850, network link 1816 and communication interface 1815. For example, a server can store requested code for an application program (e.g., a JAVA applet) on a tangible non-volatile computer-readable storage medium to which it is connected. The server can retrieve the code from the medium and transmit it through the Internet, thence a local ISP, thence a local network, thence communication interface 1815. The received code can be executed by data processing system 1810 as it is received, or stored in data storage system 1840 for later execution.

Other Exemplary Embodiments

Note that the present invention is not limited to the above-described exemplary embodiments, but can be modified as appropriate. For example, the flow rate measuring device 6 according to the second exemplary embodiment can be added to the image flow cytometer 400 according to the fourth exemplary embodiment to thereby generate a three-dimensional image by using the flow rate Vf. In this case, a distortion of a three-dimensional image to be generated can be reduced even when the flow rate Vf varies. Consequently, according to this configuration, it is possible to obtain a three-dimensional image of each microparticulate sample with high accuracy.

For example, in the image flow cytometer 400 according to the fourth exemplary embodiment, the irradiation optical system 2 and the irradiation optical system 8 can have a configuration similar to that of the irradiation optical system 7 according to the third exemplary embodiment. This enables generation of a three-dimensional image by using the flow rate Vf. In this case, a distortion of a three-dimensional image to be generated can be reduced even when the flow rate Vf varies. Consequently, according to this configuration, it is possible to obtain the three-dimensional image of each microparticulate sample with high accuracy.

Various aspects use irradiation spots smaller than a cell, or much smaller than a cell. This advantageously permits determining the internal structure of a cell. Various aspects measure microparticulate samples at a far high resolution, e.g., more than five points across a microparticulate sample, or more than ten points, or more than 100 points. This permits producing "image maps" of the microparticulate samples. These image maps include resultant-light data at various points throughout the microparticulate sample. The image map can include details of the organelle-related fluorescence or the locations of selected components of an object. A human-visible image can be determined as a representation of all or part of the image map. A 2-D image map advantageously provides much more detail than a conventional flow cytometer. Scanning in two different planes, e.g., two planes orthogonal to the flow of the stream, permits determining two 2-D image maps. These can be combined to provide a 3-D image map of the cell. this is similar to a volumetric scan, but with simpler hardware.

Various aspects are useful for hematological applications such as counting blood cells of various types. Compared to conventional COULTER COUNTERS, various aspects of image flow cytometers herein can determine many more details about each cell measured.

In various aspects, a method of performing flow cytometry includes providing a fluid flow through a flow chamber, the fluid flow carrying an object such as a microparticulate sample. Laser or other incident light is directed to form an irradiation spot smaller than the object. The irradiation spot is moved at least substantially perpendicular to the direction of the flow while the object moves with the fluid. Resultant light leaving the flow chamber is detected, e.g., transmitted light, forward-scattered light, side-scattered light, or fluorescent emissions in any direction or in a particular direction. The light can be detected by PMTs, CCDs, PIN diodes, or other light sensors. Signals corresponding to the detected light are automatically processed using a controller (e.g., control unit 5) to determine properties of the object. In various aspects, the spot-moving and light-detecting steps are repeated for a plurality of objects, and corresponding signals are processed to determine properties of the plurality of objects. In various aspects, the controller automatically produces two-dimensional views of the object(s), or plots of, e.g., forward-scattered light intensity vs. side-scattered light intensity, or histograms of, e.g., the number of objects exhibiting a particular fluorescence.

In various aspects, multiple beams of incident light are provided at different positions along a flow axis of the flow chamber. The resultant light is detected separately for each of the beams. The controller automatically processes the detected resultant light to determine a plurality of two-dimensional images, each corresponding to one beam. The controller then automatically produces a three-dimensional model of the object using the plurality of two-dimensional images. Examples of this are discussed above with reference to FIGS. 15, 16A, 16B, and 16C. In various aspects, the controller automatically produces the three-dimensional model using the detected resultant light, without first making the two-dimensional images.

In view of the foregoing, various aspects provide flow cytometers and ways of performing flow cytometry that achieve much finer resolution than prior schemes. A technical effect is to measure the shapes of microparticulate samples, such as cells, and to measure data regarding the internal structures of those samples.

From description herein, it will be apparent that embodiments can be varied in many ways. Such variations are not to be regarded as a departure from the spirit and scope of the invention, and all such modifications as would be obvious to one skilled in the art are intended for inclusion within the scope of the following claims.

The invention is inclusive of combinations of the aspects described herein. References to "a particular aspect" (or "embodiment" or "version") and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

What is claimed is:

1. An image flow cytometer for observing a microparticulate sample, the flow cytometer comprising:
   a flow chamber including a flow channel formed therein to permit the microparticulate sample to flow through the flow channel in a flow direction;
   at least one irradiation optical system adapted to:
      irradiate the microparticulate sample in the flow channel with incident light in an irradiation spot having a full width at half maximum no larger than 2 µm; and
      scan an irradiation position of the irradiation spot at least partly across the microparticulate sample in the flow channel, wherein the irradiation optical system is adapted to scan the irradiation position in a first direction along an axis substantially perpendicular to the flow direction and in a second direction along the axis opposite the first direction;
   at least one detection optical system including:
      a first photodetector adapted to provide first resultant-light data corresponding to light intensity of resultant transmitted light from the flow chamber while the irradiation position is scanned in the first direction and while the irradiation position is scanned in the second direction; and
      a second photodetector adapted to provide second resultant-light data corresponding to light intensity of resultant diffracted light from the flow chamber while the irradiation position is scanned in the first direction and while the irradiation position is scanned in the second direction; and a control unit that detects the microparticulate sample based at least in part on a change of the first resultant-light data or the second resultant-light data from the detection optical system.

2. The image flow cytometer according to claim 1, wherein the irradiation optical system is adapted to cause the incident light to converge to a diffraction limit.

3. The image flow cytometer according to claim 1, wherein the control unit is adapted to cause the irradiation optical system to scan the irradiation position so that a focal point of the incident light passes through a center of a section of the flow channel perpendicular to the flow direction of the microparticulate sample.

4. The image flow cytometer according to claim 1, wherein the detection optical system further includes a third photodetector adapted to provide third resultant-light data corresponding to light intensity of resultant side-scattered light from the flow chamber while the irradiation position is scanned in the first direction and while the irradiation position is scanned in the second direction and the control unit is further configured to detect the microparticulate sample based at least in part on a change of the third resultant-light data from the detection optical system.

5. The image flow cytometer according to claim 1, wherein the irradiation optical system includes a laser, and the incident light comprises light from the laser.

6. The image flow cytometer according to claim 5, wherein the irradiation optical system includes a light deflector that deflects the incident light substantially along the axis in order to scan the irradiation position.

7. The image flow cytometer according to claim 6, wherein the light deflector comprises an acoustic optical deflector or an electro-optic deflector.

8. A system, comprising:
a flow chamber including a flow channel formed therein to permit a microparticulate sample to flow through the flow channel in a flow direction;
at least one irradiation optical system adapted to irradiate the microparticulate sample in the flow channel with incident light in an irradiation spot, and to scan an irradiation position of the irradiation spot substantially perpendicular to the flow direction and at least partly across the microparticulate sample in the flow channel;
at least one detection optical system including:
a first photodetector adapted to provide first resultant-light data corresponding to light intensity of resultant transmitted light from the flow chamber while the irradiation position is scanned; and
a second photodetector adapted to provide second resultant-light data corresponding to light intensity of resultant diffracted light from the flow chamber while the irradiation position is scanned; and
a control unit that detects the microparticulate sample based at least in part on a change of the first resultant-light data or the second resultant-light data, wherein the control unit is adapted to:
correlate a coordinate determined from a flow rate of the microparticulate sample and a rate of the scanning to at least the first resultant-light data or the second resultant-light data; and
determine a two-dimensional distribution of at least the resultant transmitted light or the resultant diffracted light of the microparticulate sample.

9. The system according to claim 8, wherein the control unit is adapted to provide a two-dimensional image representing the two-dimensional distribution.

10. The system according to claim 8, further comprising a plurality of detection optical systems, the plurality of detection optical systems including the at least one detection optical system, and a plurality of irradiation optical systems, the plurality of irradiation optical systems including the at least one irradiation optical system, wherein:
individual ones of the plurality of detection optical systems are disposed on opposite sides of the flow chamber from respective ones of the plurality of irradiation optical systems; and
the control unit is adapted to:
determine individual ones of a plurality of two-dimensional distributions from respective ones of the plurality of the detection optical systems, the plurality of two-dimensional distributions including the two-dimensional distribution; and
produce a three-dimensional distribution of at least the resultant transmitted light or the resultant diffracted light of the microparticulate sample by combining multiple ones of the plurality of two-dimensional distributions.

11. The system according to claim 10, wherein the control unit is adapted to produce a three-dimensional image representing a three-dimensional distribution of at least the resultant transmitted light or the resultant diffracted light of the microparticulate sample.

12. The system according to claim 8, further comprising a flow rate measurement unit that measures the flow rate of the microparticulate sample and outputs a measurement result to the control unit.

13. The system according to claim 12, wherein the control unit is adapted to sequentially update the flow rate of the microparticulate sample according to the measurement result from the flow rate measurement unit.

14. The system according to claim 12, wherein the flow rate measurement unit is disposed in the flow channel or is connected to the flow channel, and observes the flow rate of the microparticulate sample flowing through the flow channel.

15. The system according to claim 12, wherein
the flow rate measurement unit includes the irradiation optical system and the control unit;
the irradiation optical system includes a phase diffraction grating that provides the incident light including a plurality of diffracted light beams;
the irradiation optical system directs the plurality of diffracted light beams to respective, different irradiation positions along the direction of flow of the flow channel; and
the control unit is adapted to calculate the flow rate of the microparticulate sample from a distance between the irradiation positions of two diffracted light beams selected from the plurality of diffracted light beams; and a time difference obtained when the microparticulate sample passes through the irradiation positions.

16. The system according to claim 15, wherein the irradiation optical system is adapted to scan the respective irradiation positions substantially along one or more axes perpendicular to the flow direction.

17. The image flow cytometer according to claim 1, wherein:
the irradiation optical system is adapted to provide the incident light including a plurality of light beams;

the irradiation optical system directs the plurality of light beams at respective, different angles to the irradiation position;

the detection optical system is adapted to provide respective, separate resultant-light data corresponding to each of the light beams; and the control unit is adapted to compute a three-dimensional image of the microparticulate sample using the detected separate resultant-light data.

18. The image flow cytometer according to claim 17, wherein the irradiation optical system includes a light source and a diffraction grating that diffracts light from the source to provide the incident light including the plurality of light beams.

19. The image flow cytometer according to claim 1, further comprising a flow-inducing device configured to provide a plurality of microparticulate samples to the flow channel, wherein:

the plurality of microparticulate samples includes the microparticulate sample;

the irradiation optical system scans the irradiation position through an irradiation volume; and the flow channel is shaped so that only one of the plurality of microparticulate samples can be in the irradiation volume at one time.

20. A method comprising:

providing a fluid flow through a flow chamber, the fluid flow carrying a microparticulate sample;

scanning an irradiation spot smaller than the microparticulate sample at least partly across the microparticulate sample in the flow chamber, wherein the scanning includes scanning the irradiation spot in a first direction along an axis substantially perpendicular to a direction of the fluid flow and in a second direction along the axis opposite the first direction;

detecting, while the irradiation position is scanned in the first direction and while the irradiation position is scanned in the second direction:

a first detection signal of resultant transmitted light; and a second detection signal of resultant diffracted light having a wavelength substantially the same as a wavelength of the irradiation spot; and determining an image map of the microparticulate sample using the first and second detection signals and a flow rate of the fluid flow.

* * * * *